(12) United States Patent
Schneider et al.

(10) Patent No.: US 6,420,338 B1
(45) Date of Patent: Jul. 16, 2002

(54) INHIBITION OF THE SRC KINASE FAMILY PATHWAY AS A METHOD OF TREATING HBV INFECTION AND HEPATOCELLULAR CARCINOMA

(75) Inventors: Robert J. Schneider; Nicola Klein, both of New York, NY (US)

(73) Assignee: New York University Medical Center, New York, NY (US)

( * ) Notice: Subject to any disclaimer, the term of this patent is extended or adjusted under 35 U.S.C. 154(b) by 0 days.

(21) Appl. No.: 08/874,430

(22) Filed: Jun. 13, 1997

(51) Int. Cl.$^7$ ........................ A61K 38/57; A61K 31/135; A61K 31/505; A61K 31/35
(52) U.S. Cl. ........................ 514/12; 514/646; 514/258; 514/789; 514/451; 514/619
(58) Field of Search ........................ 514/12, 646, 258, 514/789, 451, 619

(56) References Cited

U.S. PATENT DOCUMENTS 5,593,997 A * 1/1997 Dow et al. .................. 514/258

FOREIGN PATENT DOCUMENTS

| WO | 91/16892 | * 11/1991 |
| WO | 96/40629 | * 12/1996 |

OTHER PUBLICATIONS

Messerschmitt et al., 1997, "DNA Tumor Viruses and Src Family Tyrosine Kinases, an Intimate Relationship", Virology 227:271–280.

Stokoe and McCormick, 1997, "Activation of c–Raf–1 by Ras and Src through Different Mechanisms: Activation In Vivo and In Vitro", EMBO 16:2384–2396.

Benn et al., 1996, "Hepatitis B Virus HBx Protein Induces Transcription Factor AP–1 by Activation of Extracellular Signal–Regulated and c–Jun N–Terminal Mitogen–Activated Protein Kinases", J. Virol. 70:4978–4985.

Butel et al., 1996, "Is the DNA Repair System Involved in Hepatitis–B–Virus–Mediated Hepatocellular Carcinogenesis", Trends Microbiol. 4:119–124.

Hanke et al., 1996, "Discovery of a Novel, Potent, and Src Family–Selective Tyrosine Kinase Inhibitor", J. Biol. Chem. 271:695–701.

Lowell and Soriano, 1996, "Knockouts of Src–Family Kinases: Stiff Bones, Wimpy T Cells, and Bad Memories", Genes & Dev. 10:1845–1857.

Ramdas et al., 1996, "A Synthetic Peptidic Substrate of Minimal Size and Semi–Optimal Sequence for the Protein Tyrosine Kinase pp60$^{c-src}$", Arch. Biochem. Biophys. 326:73–78.

Su and Scneider, 1996, "Hepatitis B Virus HBx Protein Activates Transcription Factor NF–κB by Acting on Multiple Cytoplasmic Inhibitors of rel–Related Proteins", J. Virol. 70:4558–4566.

Yen, 1996, "Hepadnaviral X Protein: Review of Recent Progress", J. Biomed. Sci. 3:20–30.

Barone and Courtneidge, 1995, "Myc but not Fos Rescue of PDGF Signalling Block Caused by Kinase–Inactive Src", Nature 378:509–512.

Benn et al., 1995, "Hepatitis B Virus HBX Protein Deregulates Cell Cycle Checkpoint Controls", Proc. Natl. Acad. Sci USA 92:11215–11219.

Doria et al., 1995, "The Hepatitis B Virus HBx Protein Is a Dual Specificity Cytoplasmic Activator of Ras and Nuclear Activator of Transcription Factors", EMBO 14:4747–4757.

Erpel and Courtneidge, 1995, "Src Family Protein Tyrosine Kinases and Cellular Signal Transduction Pathways", Curr. Opin. Cell Biol. 7:176–182.

Lee et al., 1995, "Precision Substrate Targeting of Protein Kinases v–Abl and c–Src", J. Biol. Chem. 270:27022–27026.

Lee et al., 1995, "Hepatitis B Virus X Protein Interacts with a Probable Cellular DNA Repair Protein", J. Virol. 69:1107–1114.

Nair et al., 1995, "Identification of Efficient Pentapeptide Substrates for the Tyrosine Kinase pp60$^{c-src}$", J. Med. Chem. 38:4276–4283.

Ramdas et al., 1995, "A Tyrophostin–Derived Inhibitor of Protein Tyrosine Kinases: Isolation and Characterization", Arch. Biochem. Biophys. 323:237–242.

Tsui et al., 1995, "Posttranscriptional Clearance of Hepatitis B Virus RNA by Cytotoxic T Lymphocyte–Activated Hepatocytes", Proc. Natl. Acad. Sci. USA 92:12398–12402.

(List continued on next page.)

Primary Examiner—Rebecca E. Prouty
(74) Attorney, Agent, or Firm—Pennie & Edmonds LLP

(57) ABSTRACT

The present invention relates to therapeutic protocols and pharmaceutical compositions designed to target HBx mediated activation of Src kinase, members of the Src tyrosine kinase family and components of the Src kinase family signal transduction pathways for the treatment of HBV infection and related disorders and diseases, such as HCC. The invention further relates to pharmaceutical compositions for the treatment of HBV infection targeted to HBx and its essential activities required to sustain HBV replication. The invention is based, in part, on the Applicants' discovery that activation of Src kinase signaling cascades play a fundamental role in mammalian hepadnavirus replication. Applicants have demonstrated that HBx mediates activation of the Src family of kinases and that this activation is a critical function provided by HBx for mammalian hepadnavirus replication.

9 Claims, 8 Drawing Sheets

OTHER PUBLICATIONS

Figure 1A:
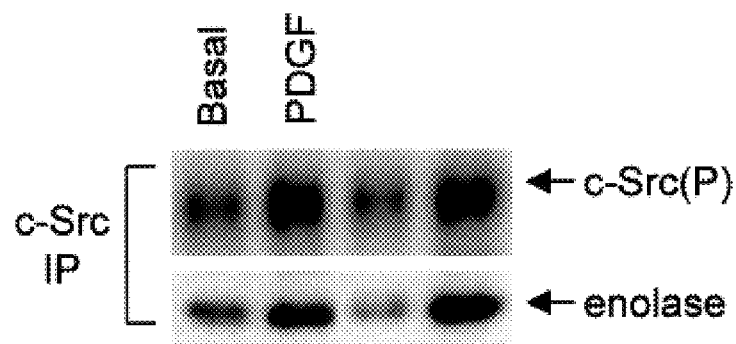

Yamaji et al., 1995, "Overexpression of csk Inhibits Acid–Induced Activation of NHE–3", Proc. natl. Acad. Sci USA 92:6274–6278.

Ye et al., 1995, "L–O–(2–Malonyl)Tyrosine: A New Phosphotyrosyl Mimetic for the Preparation of Src Homology 2 Domain Inhibitory Peptides", J. Med. Chem. 38:4270–4275.

Yokoyama et al., 1995, "Angelmicin B, a New Inhibitor of Oncogenic Signal Transduction, Inhibits Growth and Induces Myelomonocytic Differentiation of Human Myeloid Leukemia HL–60 Cells", Leuk. Res. 20:491–497.

Balsano et al., 1994, "Hepatitis B Virus X Gene Product Acts as a Transactivator In Vivo", J. Hepatol. 21:103–109.

Benn et al., 1994, "Hepatitis B Virus HBx Protein Activates Ras–GTP Complex Formation and Establishes A Ras, Raf, MAP Kinase Signalling Cascade", Proc. Natl. Acad. Sci. USA 91:10350–10354.

Murakami et al., 1994, "Transactivation of Human Hepatitis B Virus Protein, HBx, Operates through a Mechanism Distinct from Proytein Kinase C and Okadaic Acid Activation Pathways", Virology 199:243–246.

Natoli et al., 1994, "Induction of the DNA–Binding Activity of c–Jun/c–Fos Heterodimers by the Hepatits B Virus Transactivators pX", Mol. Cell. Biol. 14:989–998.

Robinson, 1994, "Molecular Events in the Pathogenesis of Hepadnavirus–Associated Hepatocellular Carcinoma", Ann. Rev. Med. 45:297–323.

Takada et al., 1994, "Interaction of Hepatitis B Virus X Protein with a Serine Protease, Tryptase $TL_2$ as an Inhibitor", 9:341–348.

Cooper and Howell, 1993, "The When and How of Src Regulation", Cell 73:1051–1054.

Cross et al., 1993, "Transactivation by Hepatitis B Virus X Protein Is Promiscuous and Dependent on Mitogen–Activated Cellular Serine/Threonine Kinases", Proc. Natl. Acad. Sci. USA 90:8078–8082.

Kekule et al., 1993, "Hepatitis B Virus Transactivator HBx Uses a Tumor Promoter Signalling Pathway", Nature 361:742–745.

Koike et al., 1993, "High–Level Expression of Hepatitis B Virus HBx Gene and Hepatocarcinogenesis in Transgenic Mice", Hepatology 19:810–819.

Liu et al., 1993, "Regulation of c–Src Tyrosine Kinase Activity by the Src SH2 Domain", Oncogene 8:1119–1126.

Twamley–Stein et al., 1993, "The Src Family Tyrosine Kinases Are Required for Platelet–Derived Growth Factor–Mediated Signal Transduction in NIH 3T3 Cells", Proc. Natl. Acad. Sci. USA 90:7696–7700.

Dent et al., 1992, "Activation of Mitogen–Activated Protein Kinase Kinase by v–Raf in NIH 3T3 Cells and In Vitro", Science 257:1404–1407.

Howe et al., 1992, "Activation of the MAP Kinase Pathway by the Protein Kinase raf", Cell 71:335–342.

Lucito and Schneider, 1992, "Hepatitis B Virus X Protein Activates Transcription Factor NF–κB without a Requirement for Protein Kinases C", J. Virol. 66:983–991.

Sawyers et al., 1992, "Dominant Negative MYC Blocks Transformation by ABL Oncogenes", Cell 70:901–910.

Maguire et al., 1991, "HBV X Protein Alters the DNA Binding Specificity of CREB and ATF–2 by Protein–Protein Interactions", Science 252:842–844.

Mahe et al., 1991, "Hepatitis B Virus X Protein Transactivates Human Interleukin–8 Gene through Acting on Nuclear kB and CCAAT/Enhancer–Binding Protein–Like cis–Elements", J. Biol. Chem. 266:13759–13763.

Rogler, 1991, "Cellular and Molecular Mechanisms of Hepatocarcinogenesis Associated with Hepadnavirus Infection", Curr. Top. Microbiol. Immunol. 168:103–140.

Seeger et al., 1991, "Woodchuck Hepatitus Virus Is a More Efficient Oncogenic Agent than Ground Squirrel Hepatitis Virus in a Common Host", J. Virol. 65:1673–1679.

Haruna et al., 1990, "Expression of X Protein and Hepatitis B Virus Replication in Chronic Hepatitis", Hepatology 13:417–421.

Lee et al., 1990, "Hepatitis B Virus Transactivator X Protein Is Not Tumorigenic in Transgenic Mice", J. Virol. 64:5939–5947.

Seto et al., 1990, "Transactivation by the Hepatitis B Virus X Protein Depends on AP–2 and Other Transcription Factors", Nature 344:72–74.

Katayama et al., 1989, "Detection of hepatitis B Virus X Gene Protein and Antibody in Type B Chronic Liver Disease", Gastroenterology 97:990–998.

Siddiqui et al., 1989, "Trans–Activation of Viral Enhancers Including Long Terminal Repeat of the Human Immunodeficiency Virus by the Hepatitis B VIrus X Protein", Virology 169:479–484.

Spandau and Lee, 1988, "Trans–Activation of Viral Enhancers by the Hepatitis B Virus X Protein", J. Virol. 62:427–434.

Cartwright et al., 1987, "Cell Transformation by $pp60^{c-src}$ Mutated in the Carboxyl–Terminal Regulatory Domain", Cell 49:83–91.

Ganem and Varmus, 1987, "The Molecular Biology of the Hepatitis B Viruses", Ann. Rev. Biochem. 56:651–693.

Popper et al., 1987, "Hepatocarcinogenicity of the Woodchuck Hepatitis Virus", Proc. Natl. Acad. Sci. USA 84:866–870.

Twu and Schloemer, 1987, "Transcriptional Trans–Activating Function of Hepatitis B Virus", J. Virol. 61:3448–3453.

Yaginuma et al., 1987, "Hepatitis B Virus (HBV) Particles Are Produced in a Cell Culture System by Transient Expression of Transfected HBV DNA", Proc. Natl. Acad. Sci. USA 84:2678–2682.

Marion et al., 1986, "Hepatocellular Carcinoma in Ground Squirrels Persistently Infected with Ground Squirrel Hepatitis Virus", Proc. Natl. Acad. Sci. USA 83:4543–4546.

Meyers et al., 1986, "Hepatitis B Virus Polypeptide X: Expression in *Escherichia coli* and Identification of Specific Antibodies in Sera from Hepatitis B Virus–Infected Humans", J. Virol. 57:101–109.

Iba et al., 1985, "Low Level of Cellular Protein Phosphorylation by Nontransforming Overproduced $p60^{c-src}$", Mol. Cell. 5:1058–1066.

Beasley et al., 1981, "Hepatocellular Carcinoma and Hepatitis B Virus", Lancet 1129–1133.

\* cited by examiner

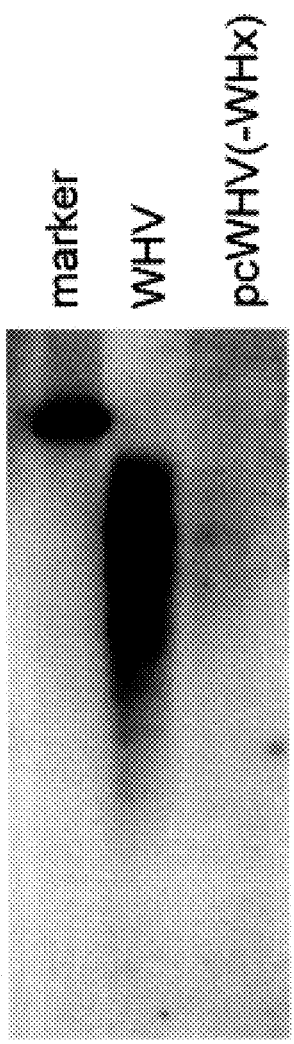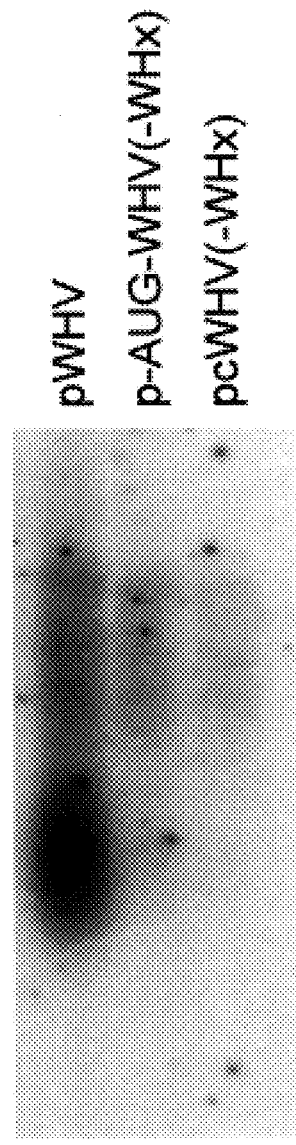
Chang Cells
FIG.4A
HepG2 Cells
FIG.4B

INHIBITION OF THE SRC KINASE FAMILY PATHWAY AS A METHOD OF TREATING HBV INFECTION AND HEPATOCELLULAR CARCINOMA

1. INTRODUCTION

The present invention relates to therapeutic protocols and pharmaceutical compositions designed to target Src family kinases and components of the Src kinase family signal transduction pathways, including HBx activation of Src kinase family signal transduction pathways for the treatment and prevention of hepatitis B virus (HBV) infection and hepatocellular carcinoma (HCC). The invention also relates to screening assays to identify potential antiviral agents which target HBx-mediated activation of Src kinase signaling cascades for the treatment of HBV.

2. BACKGROUND OF THE INVENTION

2.1 Hepatitis B Virus

Infection with HBV is an international public health problem of wide proportions. It has been estimated that at least 10% of the population of tropical Africa and Far-East Asia are chronic carriers of the virus (Tiollais et al., 1985, Nature 317:489–495). HBV is a hepatotropic virus whose course of infection can range from inapparent to acute hepatitis and severe chronic liver disease (Tiollais et al., 1985, Nature 317:489–495). Epidemiological studies have estimated that 250 million people are chronic carriers of HBV and serve as a reservoir for continued infections. Although the mechanism remains obscure, these HBV carriers have more than a 200 fold greater risk for development of hepatocellular carcinoma (HCC) (Beasley et al., 1981, Lancet 2:1129–1133).

HBV is a DNA-containing para-retrovirus that replicates by reverse transcription but comprises a separate family of viruses from retroviruses, known as hepadnaviruses. Human HBV is the prototype virus in a family that all possess a similar viral architecture and genetic arrangement, although only infection with the mammalian hepadnaviruses HBV (Tiollais et al., 1985, supra), woodchuck hepatitis B virus (WHV) (Popper et al., 1987, Proc. Natl. Acad. Sci. 84:866–870), and possibly ground squirrel hepatitis B virus (GSHV) (Marion et al., 1986, Proc. Natl. Acad. Sci. 83:4543–4546; Seeger et al., 1991, J. Virol. 65:1673–1679) cause both acute and chronic active hepatitis and HCC.

Acute hepatitis following a primary infection with HBV is usually self-limited in adults and often asymptomatic. Following acute hepatitis, 80–90% of infected adult individuals will clear viral antigens from liver and blood, resulting in clinical recovery and immunity to reinfection (Kumar et al., 1992, Basic Pathology, Fifth Edition (Philadelphia: W.B. Saunders Company)). However, 5–10% of individuals do not resolve the primary infection, instead developing a persistent hepatic infection (Ganem and Varmus, 1987, Ann. Rev. Biochem. 56:651–693). Chronic carriers represent a minority outcome following HBV infection, but constitute the majority of cases of HBV-related morbidity and mortality. Infection of infant and newborns results in a high carrier rate (approximately 90%), in contrast to infection of adults. Chronic carriers serve as the reservoir from which HBV is spread both horizontally (through blood and sexual contact) and vertically (from carrier mothers to newborns). Furthermore, chronic HBV infection frequently results in premature death from hepatic cirrhosis and liver failure (Ganem et al., 1987, Ann. Rev. Biochem. 56: 651–693). As previously noted, chronic carriers have a more than 200 fold increased risk for development of primary hepatocellular carcinoma (Beasley et al., 1981, Lancet 2:1129–1133). Because infection by HBV strongly correlates with development of HCC, considerable effort has been expended in identifying potential mechanisms for tumorigenicity by HBV (reviewed in Ganem et al. 1987, supra; Robinson, 1994, Ann. Rev. Med. 45:297–323; Rogler, 1991, Curr. Top. Micro. Immunol. 168:103–140). However, no clear mechanism has been described for the association between HCC and infection with HBV.

There are currently very limited therapeutics available for the treatment of HBV infection. Anti-HBV vaccines are currently being used to prevent HBV infection. However, the efficacy of these vaccines to treat chronic HBV infection and the availability of these vaccines to treat this worldwide health problem remains to be determined. Therefore, the need for an effective anti-HBV therapeutic still exists today.

2.2 HBx

The HBx protein is encoded by one of the four conserved open reading frames of the HBV genome. The L(+) (coding) strand encodes the four conserved open reading frames (ORFs) and codes for all the viral proteins (Ganem et al., 1987, supra). Four mRNAs have been identified. A 2.4 kb preS1 mRNA encodes the large surface antigen (pre-S1) and a 2.1 kb preS2/S mRNA encode the middle (pre-52) and small (major; S) surface antigens (Tiollais et al., 1985, supra). The 3.4 kb pregenome mRNA encodes the precore and core proteins, as well as the polymerase (P). The core protein is the principal structural component of the viral nucleocapsid and possesses nucleotide binding activity. The P protein, which has RNaseH activity, is the viral reverse transcriptase and the protein primer for synthesis of the L(−) strand (Robinson, 1994, Ann. Rev. Med. 45:297–323). The fourth mRNA is ~0.7 kb in size, and is thought to encode the transcriptional transactivator known as HBx. HBx is a conserved 154 amino acid polypeptide which corresponds to a protein of a molecular weight of ~17 kilodaltons.

The HBx protein is highly conserved within different mammalian HBV serotypes. However, in contrast to the other viral polypeptides, the role of HBx in the HBV life cycle is not yet understood. HBV-infected patient sera indicate that anti-HBx antibodies are produced (Elfassi et al., 1986, Proc. Natl. Acad. Sci. 83:2219–2222; Meyers et al., 1986, J. Virol. 57:101–109), demonstrating that expression of HBx does occur at some stage of HBV infection. HBx protein has also been detected in the livers of patients with chronic hepatitis (Haruna et al., 1991, Hepatol 13:417–421; Katayama et al., 1989, Gastroenterology 97:990–998). Patients testing positive for HBx expression have been found to have increased serum levels of HBV, thereby correlating HBx expression with increased viral replication (Haruna et al., 1991, Hepatol 13:417–421).

The precise role for HBx in the viral infectious process and in the development of HCC remains obscure. There are conflicting reports as to the role of HBx in the viral infectious process and in the development of HCC. It has been reported that there is a correlation between high levels of HBx expression and the development of HCC in transgenic mice. (Kim et al., 1991, Nature 353:317–320; Koike et al., 1994, Hepatol 19:810–819). However, these results remain controversial, as other groups have found no significant liver disease in HBx expressing mice (Balsano et al., 1994, J. Hepatol. 21:103–109; Dandri et al., 1996, J. Virol. 70; Lee et al., 1990, J. Virol. 64:5939–5947).

Several groups have shown HBx to be a largely if not entirely cytoplasmic protein, although 5–10% of HBx may reside in the nucleus (Doria et al. 1995, EMBO J. 14:4747–4757; Dandri et al. 1996 J. Virol. 70). HBx cannot be found to measurably associate with organelles, membrane vesicles or intermediate filaments, although some preferential accumulation near the cell surface can be observed (Doria et al., 1995, EMBO J. 14:4747–4757). HBx is a weak to moderately strong transcriptional transactivator. HBx has been shown to transactivate transcription of the interferon-β gene (Twu et al., 1987, J. Virol. 61:3448–3453) and of the HBV enhancer (Spandau et al., 1988, J. Virol. 62:427–434). Since those first reports, HBx has been shown to transactivate a wide variety of cellular and viral transcriptional elements (reviewed in Yen, 1996, J. Biomed. Sci. 3:20–30). Activation has been localized to specific binding sites for the transcription factors AP-1 (Benn & Schneider, 1994, Proc. Natl. Acad. Sci. 91; Natoli et al., 1994, Mol. Cell. Biol. 14:989–998; Seto et al., 1990, Nature 344:72–74), AP-2 (Seto et al., 1990, supra), NF-κB (Lucito & Schneider, 1992, J. Virol. 66:983–991; Mahe et al., 1991, J. Biol. Chem. 266:13759–13763; Su and Schneider, 1996 J. Virol. 70:4558–4566; Twu et al., 1989, J Virol. 61:3448–3453), ATF/CREB (Maguire et al., 1991, Science 252:842–844) and possibly c/EBP (Faktor and Shaul, 1990; Mahe et al., 1991, supra).

HBx does not contain any structural motifs that convincingly suggest a function, such as DNA binding (Lucito & Schneider, 1993 in Animal Viruses, L. Carrasco ed. (NY: Plenum Press) p. 67–80), nor has it been observed to directly bind DNA (Siddiqui et al., 1987, Virol. 169:479–484; Wu et al., 1990 Proc. Natl. Acad. Sci. USA 84:2678–2682). A number of activities have been ascribed to HBx including an in vitro association with p53 (Butel et al., 1996, Trend Micro. 4:119–124), an association with the human homolog of a UV-damage DNA repair protein (Lee et al., 1995, J. Virol. 69:1107–1174), and an association with a serine protease inhibitory protein (Takada et al., 1994, Oncogene 9:341–348). In summary, it appears that the activities of HBx are not limited solely to transcriptional transactivation, and surely other HBx-associated activities will be discovered.

One early model suggested that HBx indirectly stimulates transcription through activation of a protein kinase C (PKC) signaling pathway (Kekule et al., 1993, Nature 361:742–745). Many groups report PKC-independent transactivation by HBx (Benn et al., 1996, J. Virol. 70:4978–4985; Chirillo et al., 1995, J. Virol. 70; Cross et al., 1993, Proc. Natl. Acad. Sci. 90:8078–8082; Lucito & Schneider, 1992, supra; Murakami et al., 1994, Virol. 199:243–246; Natoli et al., 1994, supra). It was demonstrated that HBx activation of AP-1 and NF-κB factors occurs by HBx activation of a Ras signal transduction cascade (Benn & Schneider, 1994 supra; Cross et al. supra; Natoli et al., 1994, supra; Su & Schneider, 1996, supra). HBx was shown to stimulate RasGTP complex formation and to establish a cascade linking Ras, Raf, and MAP Kinase, which is essential for HBx activation of AP-1 (Benn & Schneider, 1994, supra) and NF-κB (Su and Schneider, 1996, supra). However, the mechanism by which HBx stimulates RasGTP complex formation remains to be elucidated. Additional results have also shown that HBx stimulates cellular proliferation in quiescent cells and induces deregulation of cell cycle checkpoint controls in a Ras dependent manner (Benn & Schneider, 1995, Proc. Natl. Acad. Sci. USA 92:11215–11219), indicating that activation of Ras by HBx appears to a play a central role in defining HBx activities.

3. SUMMARY OF THE INVENTION

The present invention relates to the treatment and prevention of HBV infection by targeting activation of the Src family of kinases. The present invention also relates to compounds which inhibit HBx-mediated activation of the Src family of kinases as well as the downstream components of the Src kinase signaling cascade for the treatment of HBV infection.

The invention is based, in part on the Applicants' surprising discovery that activation of a Src kinase signaling cascade is a critical function provided by HBx for mammalian hepadnavirus replication. The Applicants have shown that Src kinases are also activated during HBV infection of cultured cells and that this activation is an essential function of the viral HBx protein. Thus, the Applicants have demonstrated that the HBx-mediated activation of the Src kinase signaling cascade plays a fundamental role in mammalian hepadnavirus replication.

The Applicants have demonstrated that HBx mediated activation of Src kinase signaling cascade is an effective target for HBV anti-viral agents since activation of this pathway is essential for HBV replication. Therefore, targeting HBx for the treatment of HBV should result in a highly specific and efficacious method of blocking HBV replication. The Src family of kinases, although host cell gene products, are only activated in proliferating or differentiating cells, and in cells infected by many DNA and tumor viruses. Therefore, targeting the Src family of kinases for the treatment of HBV infection should result in a therapeutic with a high degree of efficacy and sufficient specificity with side effects no more toxic than chemotherapeutics currently used to treat cancer.

The present invention encompasses a variety of techniques and compounds to target the activities of HBx essential for HBV replication. In particular, these include, but are not limited to HBx-mediated activation of the Src kinase family signal transduction pathways for the treatment and prevention of HBV infection. The invention encompasses the use of known Src inhibitors to treat HBV infection. Examples of such specific inhibitors include, but not limited to: Src specific tyrosine kinase inhibitors, such as CsK, tyrphostin-derived inhibitors, derivatives of benzylidenemalonitrile, pyrazolopyrimidine PP1, and microbial agents, such as angelmicin B; and competitive inhibitors, such as small phosphotyrosine containing ligands. The invention also encompasses the use of known HBx inhibitors for the treatment of HBV, including, but not limited to, antisense RNAs directed to HBx. The present invention also relates to the use of inhibitors of downstream effectors of Src kinases, including but not limited to, cytoplasmic factors, such as Ras, Raf, focal adhesion kinase (FAK) and MAPK, and nuclear factors, such as Myc and cyclin-dependent kinases.

In another embodiment of the present invention gene therapy approaches, including dominant-negative mutants, antisense molecules and SELEX RNAs targeted to block Src kinase or HBx gene expression, may be used as a method to treat and prevent HBV infection and HCC. In yet another embodiment of the invention, upstream and downstream components and effectors of the Src kinase family signaling cascade may be targeted by gene therapy approaches to inhibit HBV infection.

The present invention further relates to screening assays to identify compounds which inhibit. HBx-mediated activation of the Src kinase signaling pathway and may be used to treat HBV infection and diseases and disorders associated with HBV infection.

The invention is illustrated by way of working examples which demonstrate that HBx mediates activation of a Src kinase signaling cascade and that activation of this signaling cascade is an essential function of HBx required to sustain HBV replication. The working examples of the present invention further demonstrate the ability of inhibitors of the Src kinase signaling cascade to inhibit HBV replication.

3.1 Definitions

As used herein, the term "target cellular gene" refers to those genes encoding members of the Src kinase family, including analogs and homologs of c-Src, Fyn, Yes and Lyn kinases and the hematopoietic-restricted kinases HcK, Fgr, LcK and Blk, and members of the Src kinase signaling pathway including both upstream and downstream components of the Src signaling cascade.

As used herein, the term "target protein" refers to those proteins which correspond to Src kinase or members of the Src kinase family or components of the Src kinase signaling pathway or proteins encoded by the HBV genome, including HBx.

As used herein, the terms "Src kinase" or "Src kinase family" refer to the related homologs or analogs belonging to the mammalian family of Src kinases, including, for example, the widely expressed c-Src, Fyn, Yes and Lyn kinases and the hematopoietic-restricted kinases Hck, Fgr, Lck and Blk.

As used herein, the terms "Src kinase signaling pathway" or "Src cascade" refer to both the upstream and downstream components of the Src signaling cascade.

As used herein, the term "to target" means to inhibit, block, or prevent gene expression, enzymatic activity, or interaction with other cellular or viral factors or contain a deletion or mutation in the catalytic or enzymatic portion of the target protein.

As used herein, the term "dominant-negative mutant" means those proteins or polypeptides which are functionally incompetent forms of the target protein and/or inhibit or modulate the enzymatic activity of the target protein or inhibit or modulate the interaction of the target protein with other cellular or viral factors.

As used herein, the term "treating or preventing HBV infection" means to inhibit the replication of the HBV virus, to inhibit HBV transmission, or to prevent HBV from establishing itself in its host, and to ameliorate or alleviate the symptoms of the disease caused by HBV infection. Treating or preventing HBV infection also encompasses inhibition of viral replication in cultured cells as well as animal hosts. The treatment is considered therapeutic if there is a reduction in viral load or viral pathogenesis, decrease in mortality and/or morbidity.

As used herein, the term "therapeutic agent" refers to any molecule, compound or treatment, for example and antiviral, that assists in the treatment of a viral infection or the diseases caused thereby or an agent which alleviates or assists in the treatment of a viral infection or the diseases caused thereby or an agent which alleviates or assists in the treatment of disorders associated with HCC.

As used herein, the term "pharmaceutically acceptable carrier" refers to a carrier medium that does not interfere with the effectiveness of the biological activity of the active ingredient, is chemically inert and is not toxic to the patient to whom it is administered.

4. BRIEF DESCRIPTION OF THE DRAWINGS

Figure 1B:
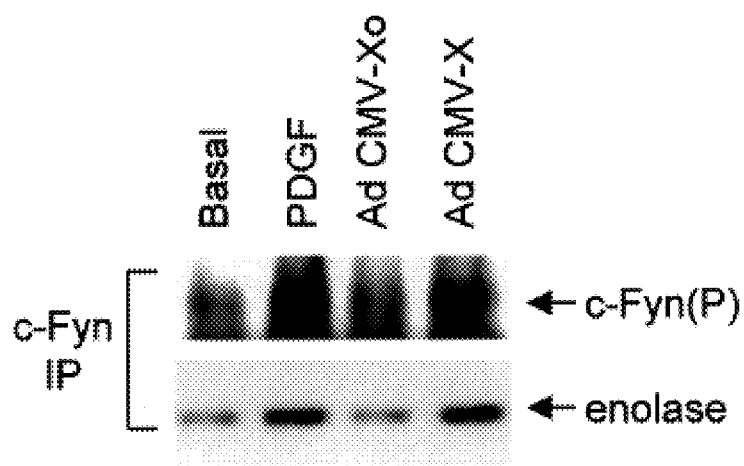
Figure 1C:
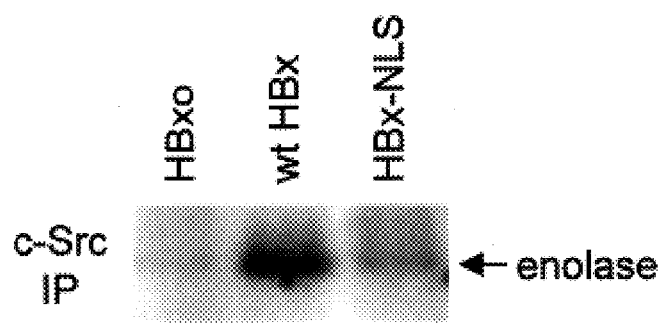

FIGS. 1A–1C Serum-starved NIH 3T3 cells were infected with AdCMV-X or -Xo viruses, c-Src or c-Fyn was immunoprecipitated, the pellet washed and assayed by incubation with the substrate enolase and [$\gamma$-$^{32}$P] ATP. Products were resolved by SDS-10%-PAGE then visualized and quantitiated by PhosphorImage analysis. c-Src (FIG. 1A) or c-Fyn (FIG. 1B) were immunoprecipitated 8 h p.i. from NIH 3T3 cell lysates expressing HBx or HBxo. Where indicated, cells were incubated with PDGF (100 ng/ml) for 5 min. (FIG. 1C) Transfected HBx activates c-Src in the cytoplasm. Chang cells were transfected with 10 $\mu$g pCMV-Xo (HBxo), PCMV-X (wt HBx) or pCMV-XNLS (nuclear HBx) expression plasmids, serum-starved for 24 h, c-Src immunoprecipitated and subjected to an in vitro trans-phosphorylation assay, then analyzed as above. Similar results were obtained with NIH 3T3 cells. (FIG. 1D, FIG. 1E) c-Src (D) or c-Fyn (E) were immunoprecipitated 3 hours p.i. from Chang cells expressing HBx or HBxo. Chang cells were stimulated with 100 $\mu$g/ml insulin (Intergen) for 10 minutes, as a positive control for Src activation (HBx mutant and HBx wildtype genes, respectively).

Figure 2A:
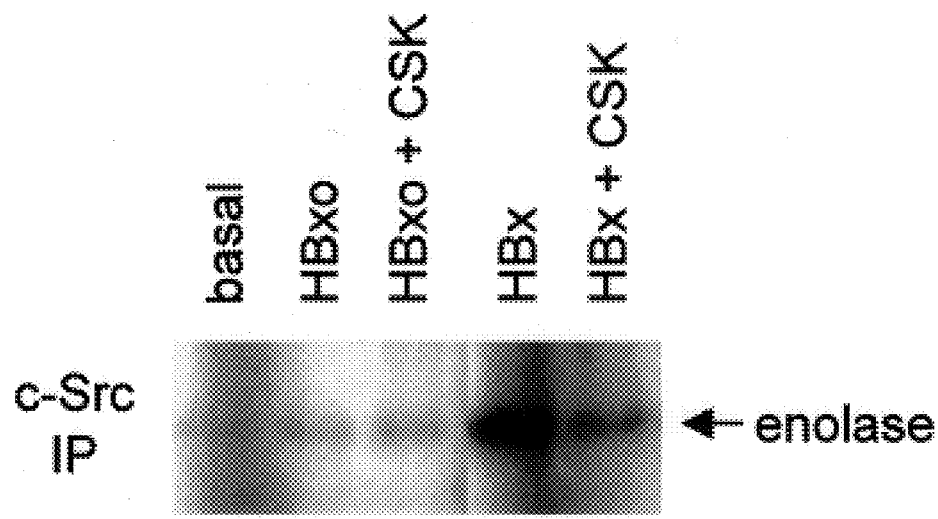
Figure 2B:
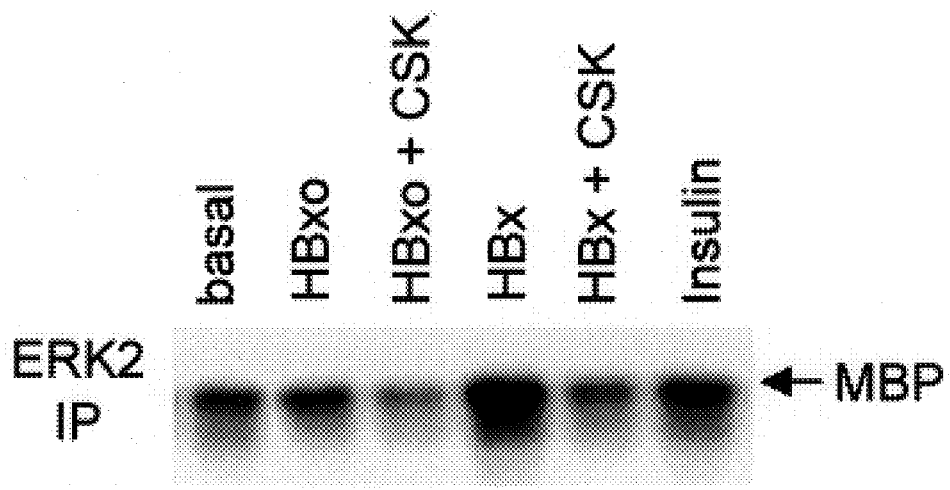

FIGS. 2A and 2B. HBx activates the Ras-MAP kinase cascade by activating the Src family of kinases. Chang cells were transfected for 18 h with 8 $\mu$g of plasmids pCMV-Xo (HBxo) or pCMV-X (wt HBx), with or without 8 $\mu$g of plasmid pCsk or carrier DNA, then serum starved for 18 h. (FIG. 2A) c-Src was immunoprecipitated from equal amounts of cell lysates and subjected to an in vitro transphosphorylation assay with [$\gamma$-$^{32}$P] ATP. (FIG. 2B) ERK2 was immunoprecipitated from equal amounts of cell lysates analyzed by in vitro phosphorylation of myelin basic protein (MBP) using [$\gamma^{32}$P] ATP. Labeled substrate proteins were resolved by SDS-15%-PAGE, then visualized and quantitated by PhosphorImage analysis. Cells were stimulated with 100 $\mu$g/ml of insulin (Intergen) for 10 min.

Figure 3A:
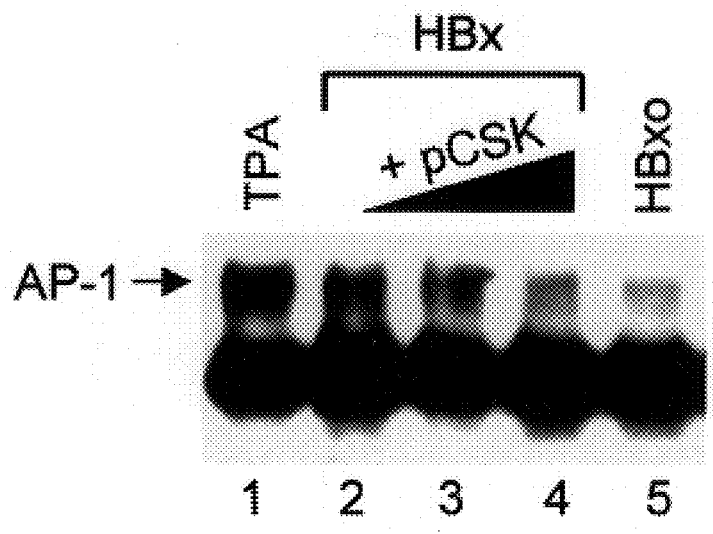
Figure 3B:
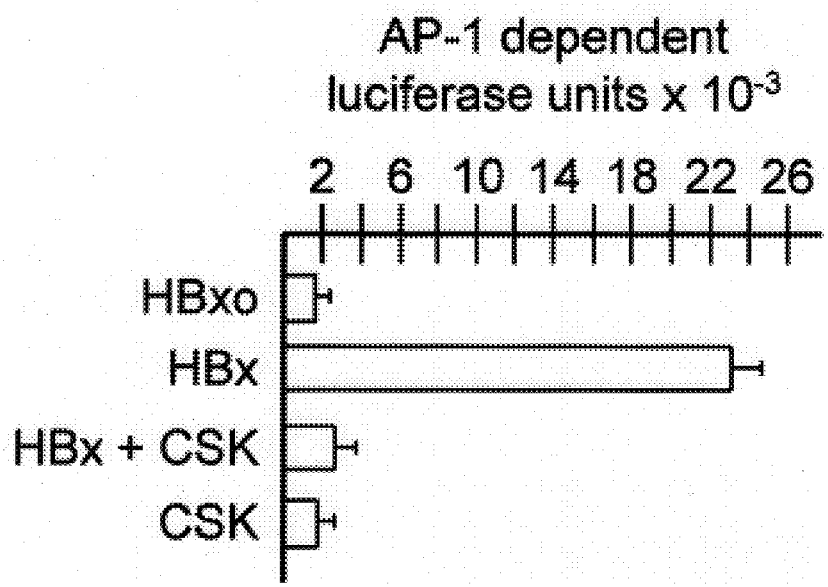

FIGS. 3A and 3B. Transcriptional activation of AP-1 by HBx involves activation of Src kinases. Chang cells transfected with 8 $\mu$g plasmids pCMV-X or pCMV-Xo, with or without cotransfection of pCsk for 18 h, then serum starved for 18 h. (FIG. 3A) Cell extracts were prepared for AP-1 EMSA as described (Benn et al., 1996, supra) using a $^{32}$P-labeled dsDNA oligonucleotide probe containing one AP-1 binding site. Reactions were carried out using 3 $\mu$g of nuclear extract, labeled oligonuleotide and 1 $\mu$g of poly(dI-dC) for 30 min at 23° C. Protein-DNA complexes were resolved by electrophoresis on 4% polyacrylamide gels and visualized by PhosphorImage analysis. As a positive control for AP-1 stimulation, cells were treated with 20 $\mu$M TPA for 30 min. (FIG. 3B) Cells were transfected as above but contained in addition 3 $\mu$g of plasmid pAP-1LUC, which encodes the luciferase reporter under the control of four AP-1 binding sites and a minimal TATA box promoter. Serum starved cells were harvested 18 h after transfection and the level of expression of the luciferase reporter assayed. Results are the average of three independent experiments.

FIGS. 4A and 4B. HBx strongly promotes prolonged WHV replication in Chang cells. (FIG. 4A) Chang cells were transfected with 20 $\mu$g of wt WHV or pcWHv (WHx mutant) plasmids, propagated for 11 days, intracellular core associated DNA purified through a 20% sucrose cushion, and viral DNA analyzed by Southern blot hybridization using a $^{32}$P-labeled full length genomic WHV probe. (FIG. 4B) HepG2 cells were transfected, intracellular core-associated RNA was purified 14 days post transfection, and viral DNA was analyzed as in (FIG. 4A).

Figure 5:
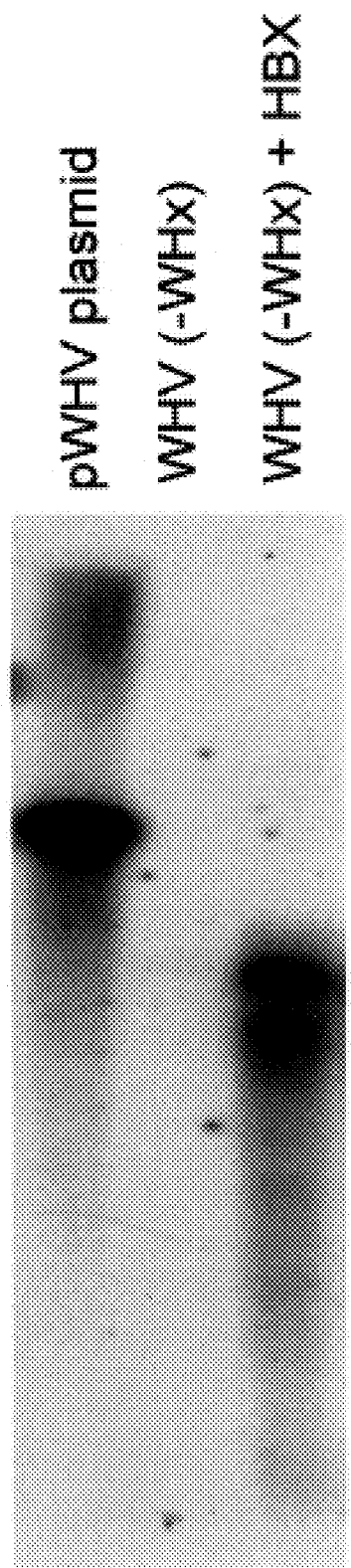

FIG. 5. trans-Complementation of defective WHV replication by HBx. Chang cells were co-transfected with 20 $\mu$g PCWHV (WHx mutant) and 10 $\mu$g of either pCMV-HBxo or pCMV-HBx. Three days post-transfection, intracellular viral core particles were isolated, and viral DNA purified. Viral DNA purified from one 10 cm plate of cells was analyzed by Southern blot hybridization.

Figure 6:
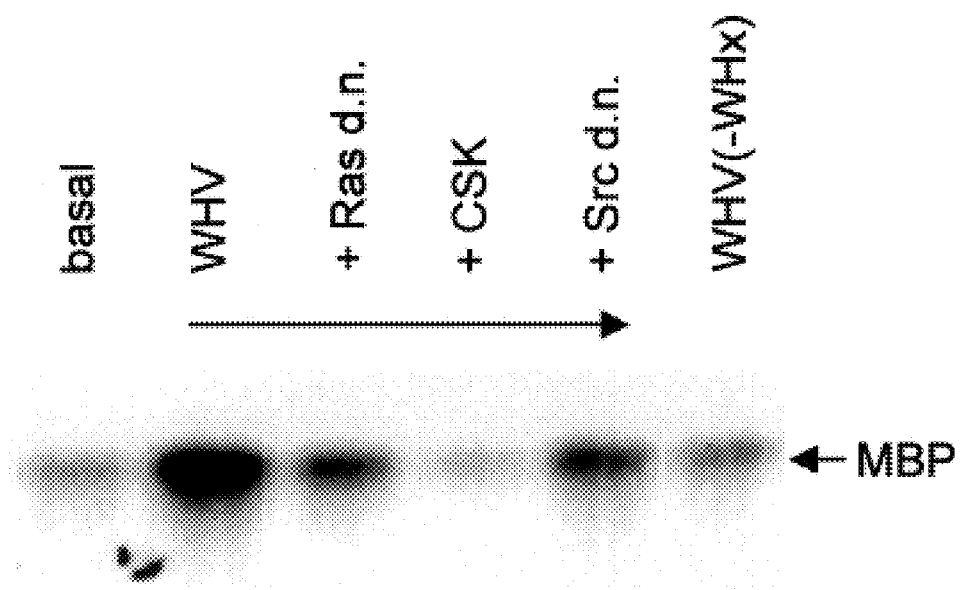

FIG. 6. Woodchuck Hepatitis B Virus (WHV) HBx protein (WHx) activates a Src-Ras signaling cascade during WHV replication in cultured cells. Chang cells were co-transfected with 20 μg pcWHV or wtWHV with 8 μg of either dominant-negative Ras, kinase inactive (dominant-negative) Src, or Csk plasmids. Eighteen hours post-transfection, cells were serum-starved in 0.5% CS for 20 hours, MAP kinase (ERK-2) was immunoprecipitated from equal amounts of cell lysates and pellets were subjected to an in vitro MBP kinase assay.

Figure 7:
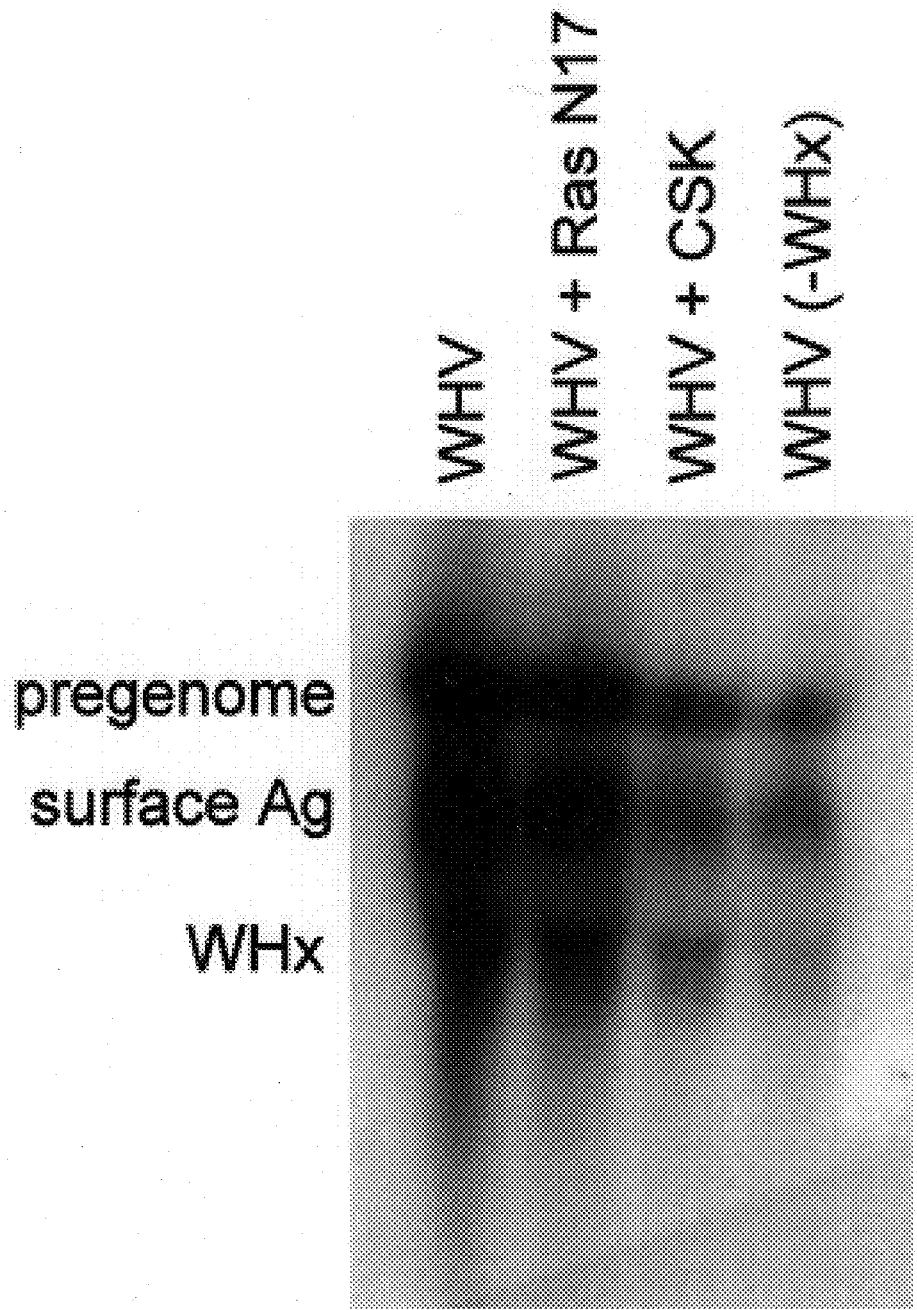

FIG. 7. WHx requires activation of Src family kinase for WHV replication. Chang cells were co-transfected with 20 μg PCWHV, wtWHV, wtWHV and RasDN (dominant-negative) (10 μg), or wtWHV and Csk (10 μg). Three days post-transfection viral core-associated DNA was isolated, purified, and subjected to Southern blot analysis using a full-length $^{32}$P-labeled WHV genomic probe.

5. DETAILED DESCRIPTION OF THE INVENTION

The present invention relates to therapeutic protocols and pharmaceutical compositions designed to target HBx-mediated activation of Src kinase, members of the Src tyrosine kinase family and components of the Src kinase family signal transduction pathways for the treatment of HBV infection and related disorders and diseases, such as HCC. The invention further relates to pharmaceutical compositions for the treatment of HBV-infection targeted to HBx and its essential activities required to sustain HBV replication.

The invention is based, in part, on the Applicants' discovery that activation of Src kinase signaling cascades plays a fundamental role in mammalian hepadnavirus replication. Applicants have demonstrated that HBx mediates activation of the Src family of kinases and that this activation is a critical function provided by HBx for mammalian hepadnavirus replication.

The present invention encompasses a variety of protocols to inhibit HBV replication and infection, including but not limited to: (1) protocols which target and inhibit HBx expression or inhibit the essential activities of HBx which may lead to activation of the Src kinase signaling cascades; (2) protocols which target and inhibit upstream effectors of the Src family of kinases, which may or may not be activated by HBx, but are required for activation of Src kinase signaling cascades; and (3) protocols which target and inhibit Src kinase family members, Src-activated enzymes and downstream effectors of Src kinases and their signal transduction pathways that are essential for viral replication.

In particular, the present invention encompasses the use of known compounds which specifically inhibit the Src family of kinases and modulate activation of the Src kinase signaling cascade, including specific Src kinase inhibitors, including, but not limited to, tyrosine kinase inhibitors, drugs, organic compounds, peptides, polypeptides and nucleotides as a method of treating HBV infection and related disorders. The present invention relates to gene therapy approaches, including dominant-negative mutants, SELEX RNAs and antisense molecules targeted to Src kinase family members, Src-activated enzymes, downstream effectors of Src kinases and their signal transduction pathways and/or HBx.

The present invention relates to cell-based and animal model based screening assays to identify novel anti-HBV agents which target HBx and its interaction and/or activation of cellular components of the Src kinase signaling cascade. In addition, the present invention relates to screening assays to identify novel antiviral agents which inhibit HBx mediated activation of Src kinase and/or downstream effectors of the Src kinase signaling cascade, such as the nuclear factor, Myc. A variety of protocols and techniques may be utilized to screen for agents which interfere with and/or inhibit the interaction and/or activation of the Src kinase signaling cascade by HBX.

The present invention further encompasses pharmaceutical compositions containing the novel agents described herein. The therapeutic modalities of the invention further encompass combination therapies in which an agent which interferes with the interaction and/or activation of the Src family of kinases by HBx, and at least one other therapeutic agent are administered either concurrently, e.g., as an admixture, separately but simultaneously or concurrently; or sequentially, including cycling therapy. Cycling therapy involves the administration of a first antiviral compound for a period of time and repeating this sequential administration, i.e., the cycle, in order to reduce the development of resistance to one of the therapies.

The novel antiviral combinations of the present invention provide a means of treatment which may not only reduce the effective dose of either drug required for antiviral activity, thereby reducing toxicity, but may also improve the absolute antiviral effect as a result of attacking the virus through multiple mechanisms. Similarly, the novel antiviral combinations provide a means for circumventing the development of viral resistance to a single therapy, thereby providing the clinician with a more efficacious treatment. Therapeutic agents to be used in combination with an agent which targets the HBx protein and its activation of Src kinase signaling cascade encompass a wide variety of known treatments, including interferon.

5.1 The Role of HBx Mediated SRC Kinase Activation in HBV-Infection and its Use as a Target for Intervention The present invention is based, in part, on the Applicants' surprising discovery that (1) HBx acts as an intracellular, cytoplasmic activator of the Src family of nonreceptor tyrosine kinases; (2) HBx stimulates tyrosine kinase activity of the Src family kinase members, including c-Src and c-Fyn; and (3) inhibition of Src activity by the expression of a Src inhibitor, e.g., the Csk protein, results in the dramatic inhibition of HBV replication. This discovery is exemplified in the in Sections 6, 7, 8 and 9 infra, which demonstrate that activation of Src kinase and the Src kinase signaling cascade is required to sustain HBV replication, and that inhibition of Src kinase dramatically inhibits HBV replication.

Applicants have demonstrated that HBx induces an increase in the tyrosine kinase activity of the Src family of kinases. The Src family of kinases, including the widely expressed Src, Fyn, Yes and Lyn kinases and the four hematopoietic-restricted kinases, Hck, Fgr, Lck and Blk (reviewed in Erpel et al. 1995 Curr. Opinion. Cell Biol. 7:176–182; Lowell et al. 1996 Genes & Devel. 10:1845–1857) are negatively regulated by phosphorylation of a carboxyterminal residue. The Src family of kinases share common structures, which include a short amino-terminal membrane anchor, a unique domain characteristic of each individual kinase, an SH2 (Src Homology-2) domain which binds phosphotyrosine residues, an SH3 (Src Homology-3) domain which binds proline-rich sequences, a catalytic domain which has kinase activity, and a short carboxy terminal tail containing the major regulatory tyrosine residue. In addition to sharing a common overall structure, Src family kinases are regulated in a similar manner. In resting cells, the Src family of kinases are found in a repressed state in which a carboxy terminal tyrosine (y) is phosphorylated (Y-527 in c-Src (Cartwright et al. 1987 Cell 49:83–19; Kmiecik et al. 1987 Cell 49:65–74)), and naturally occurring activating mutants of Src either lacks this tyrosine or are hyperphosphorylated at this site (Iba et al. 1985 Mol. Cell. Biol. 5:1058–1066). Activated Src contains an additional phosphorylated tyrosine in the catalytic domain (Y-416 in c-Src), in which appears to be a stimulatory event in vitro (Cooper et al. 1993 Cell 73:1051–1054).

In the working examples described herein, the expression of HBx resulted in an increase in the ability of Src to undergo both auto- and trans-phosphorylation. The expression of HBx also induced an increase in the tyrosine kinase activity of other Src family members, including c-Fyn.

The Applicants have further demonstrated that the expression of a Src inhibitor, i.e., the Csk protein, or dominant-negative (interfering or signaling incompetent) forms of Src and Fyn proteins resulted in the inhibition of HBx mediated activation of downstream components of the Src kinase signaling cascade. Activation of Src kinase initiates a number of downstream cascades of intracellular phosphorylation events. Activated Src results in activation of Ras, a prototypic member of the low-molecular weight family of protein GTPases which cycles between an inactive GDP-bound state and an active GTP-bound state. Activated Src also acts independently of the Ras signaling cascade to activate the nuclear factor Myc, among other proteins and kinases (reviewed in Erpel et al., 1995 supra). The formation of active Ras-GTP complexes controls a number of downstream cellular events, including opposing cellular processes, growth and differentiation (Boguski et al. 1993 Nature 366: 643–653). Active GTP-bound Ras associates and activates Raf. Activated Src has also been shown to bypass activation of Ras-GTP complexes to activate Raf in a Ras-independent manner (Stokoe & McCormick 1997 EMBO J. 16:2384–2396). Activated Raf then phosphorylates and activates Mitogen-Activated Protein Kinase Kinase (MEK) (Dent et al. 1992 Science 257:1404–1407; Howe et al. 1992 Cell 71:335–342), which in turn phosphorylates both tyrosines and threonines the extracellular-signal-regulated protein Kinases (ERKs), members of the MAP kinase (MAPK) family.

Applicants have further demonstrated that the expression a Src inhibitors, i.e., Csk protein, or dominant-negative Src or Fyn proteins resulted in the inhibition of HBx activation of downstream components of Src kinase signaling cascade. Applicants have also shown that the expression of Src dominant-negative mutants, such as Csk, inhibited the ability of HBx to stimulate activities of the nuclear factor, Myc, including stimulation of cell cycle progression by blocking HBx activation of Src kinase signaling pathways. These findings clearly establish that activation of a Src kinase signaling cascade by HBx has a critical role in the hepadnaviral life cycle.

HBx mediated activation of Src is required for HBV replication as demonstrated by way of example (Section 9 infra). The Applicants' work demonstrates that an essential component of the requirement of HBx viral replication in cultured cells is its ability to activate Src signaling cascades. HBx activation of a Src signaling cascade plays a critical role in transcriptional upregulation of the viral mRNAs. Inhibition of Src activity by the expression of a Src inhibitor, e.g., the CsK protein, results in the dramatic inhibition of HBV replication. These results illustrate that activation of Src family kinases has an essential role during HBV replicative life cycles.

The Applicants' discovery has implicated several targets for effective HBV anti-viral agents. HBV therapies that target the viral gene product HBx should result in a high degree of specificity and efficacy. HBV therapies that target the host cell gene products, the Src family of kinases, should likewise demonstrate specificity and efficacy. Although host cell gene products, the Src family of kinases are active in proliferating cells, such as cancer cells, or in virally infected cells. Therefore, targeting the Src family of kinases for the treatment of HBV infection should result in a high degree of efficacy, and sufficient specificity with side effects no more toxic than chemotherapeutics currently used to treat cancer.

5.2 Treatment of HBV-Infection Using Inhibitors of HBx Medicated Src Activation The present invention encompasses a variety of therapeutic protocols, methods and compounds to target HBx-mediated activation of the Src kinase signaling cascade for the treatment of HBV. The present invention encompasses all of the compounds described in the subsections below to target HBx-mediated activation of the Src kinase signaling cascade with the proviso that they are not known in the art to be used to treat HBV infection, including, for example, interferon α, interferon δ, interleukin-1, interleukin-2, immune-active peptides, such as thymosin-alpha, nucleoside analogs, such as vidarabine, fialuridine, lamivuridine, famciclovir, ribavarin, and corticosteroids, such as prednisone and azathioprine.

5.2.1 Compounds that Target HBx

The Applicants have demonstrated that an essential activity of HBx is the activation of Src kinase signaling cascades and that this function is required for viral replication. There are a number of mechanisms by which the multi-functional HBx protein may be exerting its effects on the Src kinase signaling cascade. The present invention encompasses targeting both direct and indirect mechanisms by which HBx is activating a Src kinase signaling cascade. HBx may be indirectly exerting its effects on the Src kinase signaling cascade through a variety of activities which have been ascribed to the protein, including but not limited to transcriptional transactivating activities, binding activity to the human homolog of the UV-damage DNA repair protein involved in nucleotide excision repair, inhibitory activities of a serine protease, and binding to the C7 subunit of the proteosome complex. The invention also encompasses targeting the activities of HBx which have yet to be elucidated which result in the activation of Src kinase signaling cascades. The activities of HBx are not limited to transcriptional transactivation and surely other HBx associated activities remain to be discovered. Therefore, not to be limited to any theory of operation, the present invention encompasses targeting any one of the activities of HBx which are involved in activation of Src kinase signaling cascades.

For example, but not by way of limitation, compounds which may be used in accordance with the present invention encompass any compound which targets HBx and inhibits its expression or interferes with its activities required for HBV replication, including but not limited to dominant-negative mutants, antisense molecules and SELEX RNAs directed to HBx. The present invention further relates to nucleotides, peptides, polypeptides, fusion proteins and other compounds which further modulate HBx activities. Other examples of compounds include, but are not limited to peptide or other compounds, including small organic and inorganic molecules directed to regions of the HBx protein that are required either directly or indirectly for HBx activation of Src signal cascades.

5.2.2 Compounds that Inhibit SRC Kinase and Downstream Effectors of the SRC Kinase Signaling Cascade A variety of techniques and compositions may be utilized to target Src kinase to inhibit its activity or to inhibit HBx mediated activation of components of the Src kinase mediated signaling cascade, thereby inhibiting HBV replication. Such techniques and compositions may include, but are not limited to, gene therapy approaches, drugs, small organic molecules identified to inhibit Src kinase, Ras, Raf, MAPK kinase, MAPK, c-Myc, cyclin-dependent kinases and/or other downstream effectors of the Src kinase signaling cascade.

In particular, compounds which may be used in accordance with the present invention to specifically target activation of Src kinase are binding proteins and competing ligands that prevent the intramolecular interaction between the carboxy-terminal phosphorylated tyrosine residue and the SH2 domain located in the amino-terminal half of the molecule and the immediately adjacent SH3 domain (Lin et al., 1993, Oncogene 8:1119–1126). In particular, compounds which may also be used in accordance with the present invention include tyrosine kinase inhibitors which block the activity the Src kinase signaling cascade and therefore would block HBV replication. Examples of such tyrosine kinase inhibitors include, but are not limited to, tyrphostin-derived inhibitors, which are derivatives of benzylidenemalonitrile, have been shown to have strong inhibitory activity of Src (Ramdas et al., 1995, Archives of Biochemistry and Biophysics 323:237–242), pyrazolopyrimidine PP1 (4-amino-5-(4-methylphenyl)-7-(t-butyl) pyrazolo [3,4-d] pyrimidine, a selective inhibitor of the Src family of kinases (Hanke et al., 1996, J. Biol. Chem. 271:695–791) and derivatives thereof. Other examples include microbial agents, such as angelmicin B, a specific inhibitor of Src tyrosine kinase activity, and derivatives thereof (Yokoyama et al., 1996, Leukemia Research 20:491–497), which may also be used to inhibit HBV replication.

In another embodiment of the present invention, small peptides which compete with larger phosphotyrosine peptides for binding to the Src kinase protein may be used to inhibit the Src kinase signaling cascade, in particular small phosphotyrosine containing peptide ligands, 5 to 6 amino acids, which are able to compete with larger phosphotyrosine-containing peptides and protein ligands for binding to SH2 domains, thereby inhibiting the Src kinase signaling cascade and blocking replication of HBV. Another embodiment of the present invention includes small peptides which correspond to catalytic or enzymatic domains of Src kinase and would compete with Src kinase, inhibiting the activation of downstream components of the Src kinase signaling cascade. Another embodiment includes the use of larger polypeptides that inhibit Src kinase activity including, but not limited to, Csk (carboxyl-terminal Src kinase) which is a specific physiologic inhibitor of Src kinase. Further examples of larger polypeptides that inhibit Src kinase activity include, for example, Src dominant-negative mutants, i.e., Srck-(Barone et al., 1995, Nature 378:509–512) and Fyn dominant-negative mutants (Twamley-Stein et al., 1993, Proc. Natl. Acad. Sci. USA 90:7696–7700), also included are dominant-negative mutants of downstream effectors of the Src kinase signaling cascade, including Ras, Raf, MAPK kinase, MAPK dominant-negative mutants and Myc dominant-negative mutants (Sawyers et al., 1992, Cell 70:901–910).

5.2.3 Antivirals to be Used in Combination With Inhibitors of SRC Kinase Pathway According to the present invention, novel antiviral agents identified by the screening methods of the present invention may be used in combination with other therapeutic agents to enhance the antiviral effect achieved. Preferably a Src kinase inhibitor is used in combination with another antiviral agent. Such additional antiviral agents which may be used with a Src kinase inhibitor include, but are not limited to, those which function on a different target molecule involved in viral replication, e.g., those which act on a different target molecule involved in viral transmission; those which act on a different loci of the same molecule; and those which prevent or reduce the occurrence of viral resistance. One skilled in the art would know of a wide variety of antiviral therapies which exhibit the above modes of activity.

In one embodiment of the invention, novel antiviral agents identified by the screening methods of the present invention are used in combination with known therapies to treat HBV infection, for example, IFN, interleukin-1, interleukin-2, immune-active peptides, nucleoside analogs and corticosteriods. The antiviral agents identified by the screening methods of the present invention may also be used in combination with exogenous or endogenous agents which induce IFN expression. In yet another embodiment, inhibitors of Src kinase are used in combination with agents which induce an anti-HBV immune response in order to target two different molecules required in the viral life cycle.

In order to evaluate potential therapeutic efficacy of Src kinase inhibitors in combination with the antiviral therapeutics described above, these combinations may be tested for antiviral activity according to methods known in the art.

A compound of the invention can be administered to a human patient by itself or in pharmaceutical compositions where it is mixed with suitable carriers or excipients at doses to treat or ameliorate various conditions involving HBV-infection. A therapeutically effective dose further refers to that amount of the compound sufficient to inhibit HBV infection. Therapeutically effective doses may be administered alone or as adjunctive therapy in combination with other treatments for HBV infection or associated diseases. Techniques for the formulation and administration of the compounds of the instant application may be found in "Remington's Pharmaceutical Sciences" Mack Publishing Co., Easton, Pa., latest addition.

5.3 Gene Therapy Approaches to Treat HBV Infection

Gene therapy approaches may also be used in accordance with the present invention to inhibit the activation of Src kinase and components of its signaling cascade. The gene therapy approaches described herein may also be applied to HBx, Src family of kinases and upstream and downstream effectors of the Src kinase signaling cascade in accordance with the present invention. Among the compounds which may disrupt the activities of HBx and its activation of the Src kinase signaling cascade are antisense, ribozyme, triple helix molecules, SELEX RNAs and dominant-negative mutants. Such molecules are designed to inhibit the expression of the target gene in HBV-infected host cells. Techniques for the production and use of antisense, ribozyme, triple helix and/or SELEX RNAs are well known to those of skill in the art and can be designed with respect to the cDNA sequence of Src kinase and components of the Src kinase signaling cascade.

5.3.1 Nucleic Acids for Gene Therapy Approaches

Antisense RNA and DNA molecules act to directly block the translation of mRNA by hybridizing to targeted mRNA and preventing protein translation. With respect to antisense DNA, oligodeoxynucleotides derived from the translation initiation site, e.g., between the −10 and +10 regions of the target gene nucleotide Ribozymes are enzymatic RNA molecules capable of catalyzing the specific cleavage of RNA. (For a review see Rossi, J., 1994, Current Biology 4:469–471). The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence see U.S. Pat. No. 5,093,246, which is incorporated by reference in its entirety. As such, within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridize with complementary oligonucleotides, using ribonuclease protection assays.

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may be introduced into cells via gene therapy methods such as those described, that do not contain sequences susceptible to whatever antisense, ribozyme, or triple helix treatments are being utilized. Alternatively, in instances whereby the target gene encodes an extracellular protein, it may be preferable to coadminister normal target gene protein in order to maintain the requisite level of target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Nucleic acids encoding dominant-negative mutants of the invention may be prepared by any method known in the art for the synthesis of DNA and RNA molecules. The dominant-negative mutants of the present invention may be produced by recombinant DNA technology using techniques well known in the art. Methods which are well known to those skilled in the art can be used to construct expression vectors containing the dominant-negative mutant gene product coding sequences and appropriate transcriptional and translational control signals. These methods are described in more detail herein.

5.3.2 Delivery of Nucleic Acids

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient for cell replacement therapy. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller & Smithies, 1989, Proc. Natl. Acad. Sci. USA 86:8932–8935; Zijlstra et al., 1989, Nature 342:435–438).

In a specific embodiment, a viral vector that contains the gene promoter suppressing nucleic acid is used. For example, a retroviral vector can be used (see Miller et al., 1993, Meth. Enzymol. 217:581–599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

In yet another specific embodiment, attenuated viruses, such as hepadnaviruses, which have the same tropism as HBV, may be engineered and used for gene therapy in accordance with the present invention. Hepadnaviruses are particularly attractive for use in gene therapy in accordance with the present invention as these viruses will deliver the therapeutic exactly to those cells infected with HBV. Hepadnaviral vectors would be particularly effective for the delivery of nucleic acids targeting components of the Src kinase signaling cascade, thereby avoiding unnecessarily knocking out expression of host genes.

Adenoviruses are other viral vectors that can be used in gene therapy. Adenoviruses are especially attractive vehicles for delivering genes to liver and respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest, 91:225–234.

Adeno-associated virus (AAV) has also been proposed for use in gene therapy (Walsh et al., 1993, Proc. Soc. Exp. Biol. Med. 204:289–300. Herpes viruses are other viruses that can also be used.

Another approach to gene therapy, for use in the cell replacement therapy of the invention, involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler & Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells (e.g., keratinocytes) may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

In an embodiment in which recombinant cells are used in gene therapy, nucleotides which encode a gene or promoter suppressor are introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

5.4 Pharmaceutical Formulations and Methods of Administration

The present invention encompasses the use of known agents which block HBx activation of Src kinase signaling cascade and novel antiviral agents identified by the screening methods of the invention in pharmaceutical compositions and therapeutic modalities for the treatment of HBV infection, and the disorders and diseases associated with HBV infection, including HCC. In one embodiment of the present invention, the novel antiviral agents identified by the screening assays of the present invention may be used in combination with other known antiviral agents to treat viral infections.

5.4.1 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer the agent of the present invention in a targeted drug delivery system, for example in a liposome targeted to the liver. The liposomes will be targeted to and taken up selectively by liver cells.

5.4.2 Composition/Formulation

The pharmaceutical compositions of the present invention may be manufactured in a manner that is itself known, e.g., by means of conventional mixing, dissolving, dragee-making, levitating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are usually known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of the Src kinases may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate, malate sales, and the like.

5.4.3 Effective Dosage

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. Such information can be used to more accurately determine useful doses in humans.

A therapeutically effective dose refers to that amount of the compound that results in a reduction in the intensity of the infection or in amelioration of symptoms or a prolongation of survival in a patient. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–90% inhibition of HCV infection using the assays described herein. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In immunization procedures, the amount of immunogen to be used and the immunization schedule will be determined by a physician skilled in the art and will be administered by reference to the immune response and antibody titers of the subject.

5.4.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

5.5 Screening Assays to Identify Novel HBV-Antiviral Agents

At least two different assay systems, described in the subsections below, can be designed and used to identify compounds or compositions that modulate HBx-mediated activation of Src kinase signaling cascades and thereby inhibit HBV replication.

The systems described below may be formulated into kits. To this end, cells expressing HBx and components of the Src kinase signaling cascade, or cells expressing components of the Src kinase signaling cascade which are capable of sustaining HBV replication, or cell lysates thereof can be packaged in a variety of containers, e.g., vials, tubes, microtitre well plates, bottles, and the like. Other reagents can be included in separate containers and provided with the kit; e.g., positive control samples, negative control samples, buffers, cell culture media, etc.

5.5.1 Cell-Based Assays

In accordance with the invention, a cell-based assay system can be used to screen for compounds that target HBx and/or HBx-mediated activation of Src kinase signaling cascades. To this end, cells that endogenously express components of the Src kinase signaling cascade, including for example, Src kinase, Ras, Raf kinase, MAPK kinase, MAPK, JNK, Myc and cyclin-dependent kinases can be engineered to express HBx under the control of an inducible promoter. Alternatively, cell lines may be engineered to express a component or components of the Src signaling cascade under the control of an inducible promoter. The cloning and characterization for each component has been described: (See, for example, Erpel et al., 1995, J. Biol. Chem. 271:16807–16812; Boquski et al., 1993, Nature 366:643–653; Bruder et al., 1992, Genes Dev. 6:545–556; Derijord et al., 1994 Cell 76:1025–1037; Miden et al, 1994 Science 266:1719–1723) each of which is incorporated by reference herein in its entirety.

The invention further encompasses cell lines, expressing both HBx and Src, either inducibly or constitutively, which results in cell cultures which may be maintained for both the short term and long term support of HBV replication. The cell lines of the present invention support HBV replication and may be maintained for long periods of time, have utility for the study of HBV replication, i.e., to identify additional cellular components required to support HBV replication, in addition to identifying potential antiviral agents for the treatment of HBV infection.

Alternately, cell lines which co-express HBx and Src kinase and components of the Src kinase signaling cascade may be genetically engineered to assay for inhibitors of HBx activation of Src. This can be engineered in cell in the absence of HBV replication or in cell lines which support the HBV life cycle as a means of (1) identifying additional factors required to support the HBV life cycle, and (2) as a system to screen test compounds, for their ability to interfere with HBx activation and/or interaction with the Src kinase, and (3) as a system to screen test compounds for their ability to inhibit Src kinase activity and therefore inhibit HBV replication.

The present invention encompasses the expression of Src kinase and components of the Src kinase signaling cascade in cell lines. In a preferred embodiment of the invention, HBx and Src kinase and components of the Src kinase signaling cascade are co-expressed in cell lines, such as human hepatoma cell lines, HepG2 and Huh7.

Methods which are well known to those skilled in the art can be used to construct expression vectors containing HBx or Src kinase gene product coding sequences and appropriate transcriptional and translational control signals. In accordance with the present invention, nucleotides encoding HBx and/or Src kinase and components of the Src kinase signaling cascade may be expressed under the control of an inducible promoter. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding Src kinase gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

In a preferred embodiment of the present invention, human Src kinase and HBx are co-expressed in hepatic cell lines, such as human hepatoma cell lines, HepG2 and Huh7, and Chang liver cells. A number of selection systems well known to those skilled in the art may be used to successfully engineer cell lines which express the Src kinase and HBx gene products. Appropriate cell lines or host systems can be chosen to ensure the correct modification of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38 cell lines.

In a preferred embodiment of the in vitro screening methods of the present invention, test methods rely on measurements of Src kinase activity or by measuring the activity of downstream effectors of Src kinase, such as MAP kinase and Myc. The assays of the present invention may include in vitro kinase assays which measure the effects of test compounds on individual components of the Src kinase signaling pathway. For example, but not by way of limitation, these assays may involve measuring the effects of a test compound on a reaction mixture containing a cell lysate prepared from HBV infected cells treated with the test compound. Src kinase may be immunoprecipitated from the cell lysate and c-Src autophosphorylation or enolase transphosphorylation activity of the immunoprecipitated kinase may be determined. MAP kinase or another component of the Src Kinase pathway may be immunoprecipitated from the cell lysate and its kinase activity measured using a known substrate of the kinase, i.e. myelin basic protein or transcription factors AFT-2, CHOP, HSP27 and Max. The activity of the MAP kinase will be determined as a measurement of the phosphorylated state of the substrate. In order to test a compound for inhibitory activity, the reaction mixture is prepared in the presence and absence of the test compound. Control reaction mixtures are incubated without the test compound or with a placebo. The lack of phosphorylation of the substrate indicates that the MAP kinase is inhibited indicating that the Src kinase signaling pathway is blocked.

In yet another embodiment of the invention, the ability of a test agent to inhibit HBx activation of Src's induction of downstream effectors may be measured. For example, activation of Src kinase signaling cascade leads to enhanced expression of Myc proteins. Therefore, activation of Myc promoter elements may be used to determine the potential anti-HBV activity of the test agent. Constructs encoding the Myc promoter region linked to any of a variety of different reporter genes may be introduced into cells expressing the Src kinase and/or components of the Src kinase signaling cascade. Such reporter genes may include but is not limited to chloramphenicol acetyltransferase (CAT), luciferase, GUS, growth hormone, or placental alkaline phosphatase (SEAP). Following exposure of the cells to the test compound, the level of reporter gene expression may be quantitated to determine the test compound's ability to regulate receptor activity. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemilumenscent assays such as those described in Bronstein, I. et al. (1994, Biotechniques 17: 172–177). Such assays provide a simple, sensitive easily automatable detection system for pharmaceutical screening.

In yet another embodiment of the invention, measurements of the tyrosine phosphorylated state of Src may be used to measure the effects of test compounds on the Src kinase signaling pathway. In resting cells, the Src family of kinases are found in a repressed state in which a carboxy terminal tyrosine (Y) is phosphorylated (Y-527 in c-Src).

Active Src is hypophosphorylated at this residue, therefore, phosphorylation of this residue of c-Src in response to a test agent may indicate the ability of that test agent to inhibit c-Src activation. Activated Src contains an additional phosphorylated tyrosine in the catalytic domain (Y-416 in c-Src), which appears to be a stimulatory event in vitro (Cooper et al., 1993, Cell 73:1051–1054). Therefore, dephosphorylation of this residue of c-Src in response to a test agent may indicate the ability of that test agent to inhibit c-Src activation.

In a particular embodiment, the target substrate can be prepared for immobilization using recombinant DNA techniques routinely used in the art. The target substrate may be for example, a region of Src containing the carboxy terminal tyrosine residue or a region of MAPK containing the tyrosine residue. For example, the target gene coding region can be fused to a glutathione-S-transferase (GST) gene using a fusion vector, such as pGEX-5-1, in such a manner that its conformation is maintained in the resulting fusion protein. In such an assay, e.g., the target gene fusion protein can be anchored to glutathione-agarose beads. The activated or infected cell lysate can be added in the presence or absence of the test compound in a manner that allows the kinase reaction to occur in the presence of $^{32}$P-ATP. At the end of the reaction period, unbound material can be washed away, and the substrate assayed for its phosphorylated state. The interaction between the target gene protein and the Src kinase pathway component can be detected by measuring the amount of radioactivity that remains associated with the glutathione-agarose beads. A successful inhibition of the interaction by the test compound will result in a decrease in measured radioactivity.

In another embodiment of the cell-based assays of the present invention, activation of Src kinase signaling cascades mediated by HBx may be measured by a viability assay to positively test for effective compounds. For example, a test compound may be applied to cells expressing HBx and Src kinase signaling components. Then an agent which induces cell death in response to activated Src kinase, such as tumor necrosis factor (TNF), is applied to cells. If the test compound is ineffective in inhibiting HBx mediated activation of Src kinase, the cells die. Compounds effective in inhibiting activation, result in cell viability. Such an assay system provides a quick and easy read-out to determine the effectiveness of a test compound to inhibit HBx mediated activation of Src kinase.

Alternatively, activation of Src kinase signaling pathways mediated by HBx may be measured by the secretion of mature HBV viral particles into the medium of growing Chang cells. For example, Chang liver cells may be stably transformed with an HBV or WHV pregenome, or with a head-to-tail dimer of either HBV or WHV genomes. The integrated virus will produce and secrete HBV/WHV particles into the medium. As demonstrated by the Applicants, the secretion of viral particles is strongly enhanced by HBx protein activation of Src kinases. If the test compound is effective in inhibiting HBx activation of Src, it will result in reduced secretion of HBV/WHV particles into the medium. The level of particle secreted into the medium can be assayed using commercial ELISA kits to detect the presence of HBV/WHV HBcAg and HBsAg.

Alternatively, the activation of Src kinase signaling pathways mediated by HBx may be measured in fission yeast, *Schizosaccharomyces pombe*. Src kinase have not been found in single cell lower eukaroytes such as yeast, and their expression induces cell death of the fission yeast (Erpel, T., Superti-Furga, G. & Courtneidge, S. A., 1995, EMBO J. 14:963–975). Studies have shown that yeast cell viability is maintained only by inhibition of Src activation, for instance, by coexpression with the Src inhibitor Csk (Koegl, M., Courtneidge, S. A. & Superti-Furga, G. 1996, Oncogene 11:2317–2329). Therefore, a viability assay is based on the fact that activation of Src kinase by HBx protein in yeast will result in cell death, whereas the inhibition of Src kinase will permit cells to grow and reproduce. *S. pombe* can be transformed with the c-Src gene and the HBx gene under the control of regulated promoters. A variety of regulated promoters can be chosen, such as the thiamine repressible nmt 1 promoter. Removal of thiamine from the medium will result in induction of both HBx and c-Src proteins, and subsequent killing of cells. If a test compound is effective in inhibiting HBx activation of Src, it will block the growth arrest.

5.5.2 Animal Model Screening Assays

The present invention relates to animal model screening assays to identify compounds effective to inhibit HBV replication. In accordance with these animal model screening assays, the present invention encompasses the expression of Src kinase and components of the Src kinase signaling cascade with or without the co-expression of HBx.

Animals of any species, including, but not limited to, woodchucks, mice, rats, rabbits, guinea pigs, pigs, micropigs, goats, and non-human primates, e.g., baboons, monkeys, and chimpanzees may be used to generate HBx and Src kinase transgenic animals.

Any technique known in the art may be used to introduce the HBx and Src kinase gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

In preferred embodiment of the invention, Src kinase is expressed alone in transgenic Src knock-out mice and a HBV pseudovirus is used to infect the animals. For example, a HBV pseudovirus which contains the HBV virus and an envelope protein from a virus with a natural tropism for murine cells, such as the murine leukemia virus (MLV), is used to bypass internalization of the HBV virus by the murine cells. These murine cells can then support the life cycle of the internalized HBV virus, because they express human Src kinase.

In one embodiment of the animal model screen of the present invention, test compounds may be administered to transgenic animals and their ability to inhibit HBV replication directly measured. For example, but not by way of limitation, these assays may involve measuring the effects of test compounds on viral replication in host cells and transgenic animals. HBV replication may be measured by a number of criteria, including measuring viral DNA. Intracellular core-associated DNA may be purified and analyzed by southern blot hybridization to measure synthesis of viral DNA replicative intermediates. The synthesis of viral DNA replicative intermediates in the presence of test compounds may be compared to levels of viral DNA replicative intermediates in the absence of the test compounds. Levels of HBV replication in the presence or absence of test compounds may also be determined by measuring levels of extracellular virus which is released or intracellular viral transcripts and/or viral proteins, including the surface antigen and the polymerase protein, using standard molecular biological techniques and methods known to those of ordinary skill in the art.

In yet another embodiment of the animal model screens of the present invention, the effect of test compounds to inhibit HBV-replication may be measured indirectly. For example, transgenic mice may be engineered which express (1) the HBx gene product under the control of an inducible promoter, and (2) readout vector which is responsive to Src activation. The readout vector may comprise a reporter gene under the control of a Myc promoter. Such reporter constructs are described in Section 5.5.1 infra. In this assay system, expression of the HBx gene product is induced and the test compound is administered to the mice. The ability of the test compound to inhibit HBx mediated activation of Src kinase and HBV replication is assayed by measuring the reporter gene. Such reporter genes may include but are not limited to chloramphenicol acetyltransferase (CAT), luciferase, GUS, growth hormone, or placental alkaline phosphatase (SEAP). Following exposure of the animal to the test compound, the level of reporter gene expression may be quantitated from the blood or tissue sample to determine the test compound's ability to regulate receptor activity. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemilumenscent assays such as those described in Bronstein, I. et al. (1994, Biotechniques 17: 172–177). Such assays provide a simple, sensitive easily detection system for pharmaceutical screening.

6. EXAMPLE

HBx is an Intracellular Activator of SRC Kinase and Downstream Components of the SRC Signaling Cascade The following studies demonstrate that HBx activates the Src family of nonreceptor tyrosine kinases. These studies also demonstrate that activation of Src fundamentally mediates HBx activation of Ras signaling and cell cycle progression.

6.1 Materials and Methods

Cell Culture

Cell lines used in this study were obtained from the American Tissue Type Culture Collection. Chang liver, NIH 3T3, and 293 cells were propagated in Dulbecco's modified Eagle's medium (DMEM) supplemented with 10% bovine calf serum (CS) and 50 mg/ml gentamycin sulfate. HepG2 cells were propagated in DMEM supplemented with 10% fetal CS. Serum starvation of Chang cells was carried out in 0.05% CS for 24–48 hours, and for NIH 3T3 cells, in 0.5% CS for 16–20 hours.

Transfections and Adenovirus Infections

Chang cells were transfected by the calcium phosphate precipitation technique (Wigler et al., 1979 Proc. Natl. Acad. Sci. 76:1373–1376). $6 \times 10^5 - 7.5 \times 10_5$ Chang cells per 10 cm plate were transfected for 7–10 hours (20 µg DNA total), after which the media was aspirated and replaced with fresh 10% CS/DMEM (Doria et al., 1995 EMBO J 14:4747–4759). Eighteen hours after transfection, Chang cells were serum starved either in 0.05% CS for 16–20 hours followed by addition of 2% serum for 2 hours to allow protein synthesis, or serum starved in 0.5% CS for 24 hours and then harvested. NIH 3T3 cells were transfected by the calcium phosphate technique overnight, serum starved in 0.5% CS for 18 hours and infected with the recombinant adenoviruses (described below).

NIH 3T3 cells were plated at $1 \times 10^6$ cells/10 cm plate and serum starved the next day in 0.5% CS for 16–18 hours. Chang cells were also plated at $1 \times 10^6$ cells/10 cm plate and serum starved in 0.05% CS for 24–48 hours. Cells were infected with AdCMV-X or AdCMV-Xo viruses at 25 pfu for 1 hour in 1 ml of PBS/2% CS, after which 10 ml of 10% CS/DMEM was added and the cells harvested at the indicated times.

The replication-defective recombinant adenoviruses express, under the control of the CMV promoter, either wild type HBx (AdCMV-X) or a mutated HBx mRNA in which all the AUGs have been mutated (AdCMV-Xo). The construction of the recombinant adenoviruses, AdCMV-X and AdCMV-Xo, have been previously described (Doria et al., 1995, supra). Viruses were propagated and titered in 293 cells before use.

Antibodies and Plasmids

Ras-specific monoclonal antibody Y13-259. (Santa Cruz Biochemicals, Inc.). Rabbit anti-Shc and anti-Sos serum. (Santa Cruz Biochemicals, Inc.). Rabbit anti-Grb2, anti-ERK2, anti-Csk, anti-JNK and anti-N-Myc were purchased from Santa Cruz. Anti-Src (M327) antibodies were purchased from Oncogene Science. Anti-Fyn antibodies (Santa Cruz) were a gift of D. Littman (NYU). Anti-phophotyrosine (4G10; UBI) and rabbit anti-p34cdc2 serum and Rabbit anti-RPTPα serum. (Upstate Biotech Inc.).

Plasmid phSos expresses human hSos under the CMV promoter plasmid pCaCSK expresses the CSK gene under the control of the CMV promoter. Plasmid pSRC expresses c-Src under the control of the CMV promoter. Plasmids pCMVSK- and PCMVFK- express the kinase-inactive (dominant-negative) forms of Src (SK) and Fyn (FK) under the control of the SV-40 LTR, respectively (Twamley-Stein et al., 1993 Proc. Natl. Acad. Sci. 90:696–700). For the present studies, the cDNAs for the kinase-inactive forms of Src and Fyn were subcloned into pcDNA1Amp (Invitrogen) for expression under the control of the CMV promoter. To create pCMVSK- (containing the dominant-negative Src under the control of the CMV promoter), a BamH1/Sal1 fragment containing the entire kinase-inactive Src was ligated into BamH1/Xho1 sites in pcDNA1Amp. To create pCMVFK- (containing the dominant-negative Fyn under the control of the CMV promoter), a BamH1 fragment containing the entire kinase-inactive Fyn was ligated into the BamH1 site of pcDNA1Amp. Plasmids wtWHV expresses the wild-type WHV genome. Plasmids pAUGWHV and pcWHV expresses WHV genome with mutations that ablate WHx expression (Seeger et al. 1991 J. Virol. 65:1673–1679). Plasmid pAUGWHV contains a mutation in the first AUG of the X open reading frame (ORF) plasmid pCWHV contains a stop codon between the second and third AUG in the X ORF (Zoulim et al., 1994, J. Virol. 68:2026–2030).

pCMV-X expresses wild-type HBx under the control of the CMV promoter. pCMV-Xo contains a mutant HBx gene in which all of the AUGs in the ORF have been mutated to GUG and therefore a functional HBx protein cannot be translated from the MRNA (Doria et al., 1995, supra). HBx-NLS contains a functional nuclear localization signal and exclusively relocates HBx protein to the nucleus, whereas HBx-SLN expresses a mutated NLS signal and is a cytoplasmic protein (Doria et al., 1995, supra). The expression vectors pCMV-HBx-NLS and pCMV-HBx-SLN were constructed by replacing the adenovirus major late promoter with the CMV promoter in the vectors pAd-HBx-NLS and pAd-HBx-SLN by ligating an EcoR1/Sal1 fragment from pCMV3C containing the CMV promoter and the adenovirus tripartite leader into the corresponding EcoR1/Sal1 sites in pAd-HBx-NLS/SLN.

Immunoprecipitation and Western Immunoblotting

Cells were lysed in 1% Triton, 20 mM Hepes pH 7.4, 150 mM NaCl, 10% Glycerol, 1 mM $Na_3VO_4$, 50 mM NaF, 1 mM PMSF, 10 µg/ml aprotinin, and 10 µg/ml leupeptin. Equal amounts of protein were immunoprecipitated on ice for 2 hours and the immune complexes were collected by incubation with protein A-agarose (Santa Cruz) for 60 minutes at 4° C. Immunoprecipitates were washed three times with HNTG (20 mM Hepes pH 7.4, 150 mM NaCl, 0.1% Triton, and 10% Glycerol), resuspended in Laemmli sample buffer, heated to 95° C. for 10 minutes, resolved by electrophoresis on SDS-polyacrylamide gels, and immunoblotted to nitrocellulose using standard techniques (Harlow and Lane, 1988, Antibodies: A Laboratory Manual (Cold Spring Harbor, N.Y.; CSH Laboratory Press)). Immunoblots were visualized using the ECL chemiluminescence system (Amersham).

Kinase Assays

To assay for MAP kinase activity, cells were lysed in freshly prepared lysis buffer (10 mM Tris HCl pH 7.5, 1% Triton X-100, 0.5% NP-40, 1 mM EDTA, 1 mM EGTA, 1 mM $Na_3VO_4$, 50 mM NaF, 1 mM PMSF, 40 mM PPi, 10 µg/ml aprotinin, and 10 µg/ml leupeptin) and MAP kinase was immunoprecipitated using 1 µg/ml anti-ERK2 antibodies from equal amounts of protein. After 4 washes with lysis buffer, and 2 with kinase buffer (20 mM Hepes pH 7.4, 10 mM $MgCl_2$), the immunoprecipitates were incubated with kinase buffer including 0.5 mg/ml myelin basic protein (MBP, Sigma), 10 mM ATP and 5 µCi [γ-$^{32}$P]ATP for 30 minutes at 30° C. The reactions were stopped by the addition of 2×sample loading buffer (Sambrook et al. 1989, supra), resolved by 15% SDS-PAGE and visualized by autoradiography. Assays for activation of JNK MAP kinases were carried out exactly as described above, except that the immunoprecipitated JNK was incubated with 5 µg purified GST-c-Jun (Benn et al., 1996, supra) and 10 µCi [γ-$^{32}$P]ATP, and resolved by 10% SDS-PAGE.

Src kinase assays were carried out essentially as described (Kypta et al., 1990, Cell 62:481–492). Briefly, NIH 3T3 or Chang cells were lysed in buffer containing 1% NP-40, 150 mM NaCl, 20 mM Tris HCl pH 8, 2.5 mM EDTA, 1 mM $Na_3VO_4$, 50 mM NaF, 1 mM PMSF, 10 µg/ml aprotinin, and 10 µg/ml leupeptin. Src and Fyn kinase activity were measured by immunoprecipitating either Src (1 µg anti-Src antibodies) or Fyn (1 µg/ml anti-Fyn antibodies) from equal amounts of cell lysate. The immunoprecipitates were washed four times with lysis buffer, once with 20 mM Hepes pH 7.4 and once with kinase buffer (20 mM Hepes pH 7.4, 10 mM $MnCl_2$). Immunoprecipitates were then resuspended in kinase buffer containing 0.2 µg acid denatured enolase (rabbit muscle; Sigma) and 20 µCi [γ-$^{32}$P]ATP or 1 µg Src-specific substrate peptide (Upstate Biotechnology), 10 mM ATP and 10 µCi [γ-$^{32}$P]ATP and incubated at 30° C. for 30 minutes. Kinase reactions containing enolase were stopped with 2×sample loading buffer, heated for 10 minutes at 95° C., and resolved by 10% SDS-PAGE. For the reactions containing the Src peptide substrate, TCA was added to a final concentration of 20%, an aliquot was spotted onto phosphocellulose paper (UBI), the filters were washed 3×5 minutes in 0.75% phosphoric acid and once in acetone, dried and analyzed by scintillation counting. Triton X-100 fractionation prior to Src kinase assays were carried out as described (Clark et al., 1993, Moll. Cell Biol. 13:1863–1871).

To assay for p34 cdc2 kinase activity, Chang cells were lysed in 1% Triton, 20 mM Tris HCl pH 8, 10 mM EDTA, 5 mM $MgCl_2$, 1 mM $Na_3VO_4$, 50 mM NaF, 1 mM PMSF, 10 µg/ml aprotinin, and 10 µg/ml leupeptin. p34 cdc2 protein was immunoprecipitated from equal amounts of cell extract, washed four times with lysis buffer, twice with kinase buffer (50 mM Hepes pH 7, 10 mM $MgCl_2$, 5 mM $MnCl_2$, 4 mM dithiothreitol [DTT]), resuspended in kinase buffer containing 50 µg/ml Histone H1 (Boehringer-Mannheim) and 5 µCi [γ-$^{32}$P]ATP, and incubated at 30° C. for 30 minutes. After stopping the reactions with sample loading buffer, the reactions were resolved by 12% SDS-PAGE, visualized by autoradiography, and quantitated by PhosphorImager analysis as described above.

Preparation of Nuclear Extracts

Nuclear extracts were prepared according to a modified Dignam protocol (Su and Schneider, 1996). Cell pellets were resuspended in 250 µl of cold Buffer A (10 mM Hepes pH 7.9, 1.5 mM $MgCl_2$, 10 mM KCl, 0.5 mM DTT, 1 mM PMSF, 10 µg/ml leupeptin and 10 µg/ml aprotinin), swollen on ice for 10 min, vortexed for 10 sec, and centrifuged for 10 sec at 12,000×g. Nuclear pellets were resuspended in 30 µl cold buffer C (20 mM Hepes pH 7.9, 25% glycerol, 420 mM NaCl 1.5 mM $MgCl_2$, 0.2 mM EDTA, 1 mM DTT, 1 mM PMSF, 10 µg/ml leupeptin and 10 µg/ml aprotinin), incubated on ice for 20 min and nuclear extracts obtained by centrifugation at 12,000×g for 2 min at 4° C.

6.2 Results

Figure 1D:
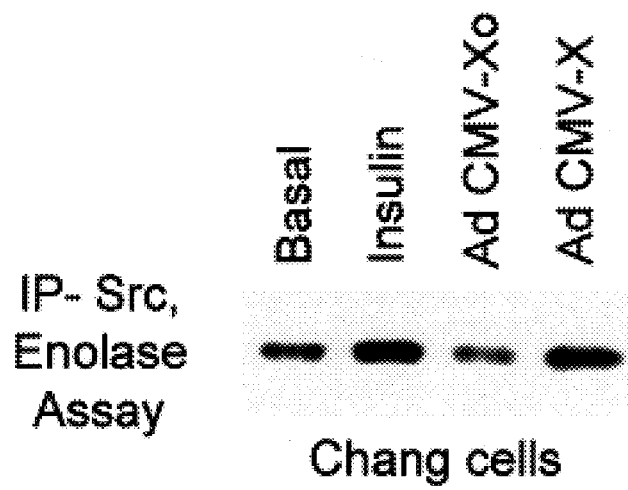
Figure 1E:
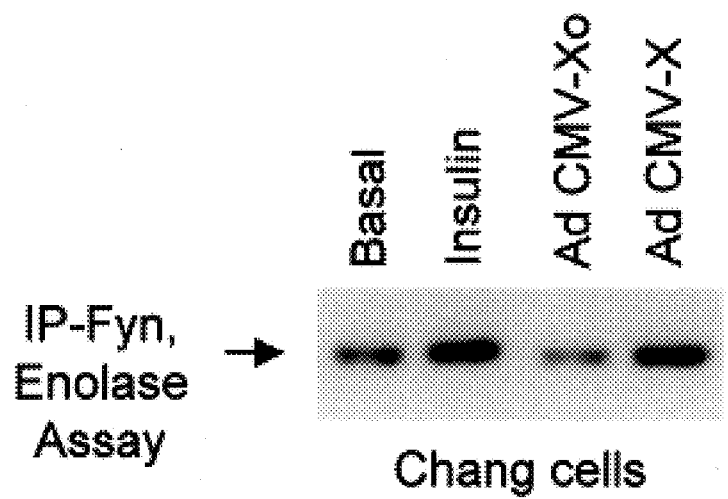

To determine whether HBx induces an increase in the tyrosine kinase activity of the Src family of kinases, serum-starved NIH 3T3 cells were infected with recombinant adenoviruses (Ad) expressing either wild-type HBx (AdCMV-X) or a mutant HBx gene which transcribes a mRNA lacking all AUGs, and is therefore not translated (AdCMV-Xo). These vectors allow for rapid delivery of HBx genes and do not activate Ras in the absence of HBx (Benn & Schneider, 1994, supra). c-Src was immunoprecipitated from an equal amount of extracted cell protein 8 hours post-infection (p.i.), the immune complex pellets were washed extensively, and an in vitro kinase assay was carried out using immunoprecipitated c-Src (auto-phosphorylation) and enolase (trans-phosphorylation) as substrates (FIG. 1A). Expression of HBx, but not HBxo, induced a specific 3–4 fold increase in the ability of Src to undergo both auto- and trans-phosphorylation. Stimulation of cells with PDGF for minutes, a prototypic Src induction protocol, induced a similar 3–4 fold activation. The observed PDGF-induced activation of c-Src is comparable to that reported by other groups (Gould and Hunter, 1988, Moll. Cell Biol. 8:3345–3356, Kypta et al., 1990, supra) and indicates that HBx expression induced activation of c-Src to an extent similar to that detected following treatment with PDGF. Identical trans-phosphorylation results were observed in Chang cells (FIG. 1D). To determine whether HBx also activates other Src family members, serum-starved NIH 3T3 cells (FIG. 1B) were infected with AdCMV-X or AdCMV-Xo viruses, c-Fyn was immunoprecipitated from equal amounts of cell lysates, and the immunoprecipitated pellets were subjected to an in vitro auto-phosphorylation and trans-phosphorylation kinase assay with the substrate enolase (FIG. 1B). Expression of HBx induced an increase in the tyrosine kinase activity of c-Fyn, comparable to activation of Fyn following PDGF (FIG. 1B) and insulin stimulation (FIG. 1E), which was not observed in the HBxo-expressing cells. Identical trans-phosphorylation results were observed in Chang cells (FIG. 1E). These data demonstrate that HBx induces the activation of different members of the Src family of nonreceptor tyrosine kinases.

To ensure that the activation of Src was not an unforseen consequence of infection with the recombinant Ads, and to determine whether HBx activates c-Src in the cytoplasm or nucleus, Chang cells were transfected with plasmids expressing either wild-type HBx, mutant HBxo, or the nuclear-targeted variant HBXNLS. HBX-NLS contains a functional nuclear localization signal which causes the protein to become exclusively relocated to the nucleus. Following transfection, cells were serum-starved for 24 h, c-Src was immunoprecipitated from equal amounts of cell lysate, and an in vitro kinase assay was carried out using enolase as a trans-phosphorylation substrate (FIG. 1C). Src kinase activity was strongly activated in serum-starved cells expressing wild-type HBx for 24–36 h, but not in those expressing HBxo or HBx-NLS. These results are consistent with the ability of HBx to activate Ras signaling cascades only in the cytoplasm. They also confirm that it is HBx which activates c-Src, and that a cytoplasmic location is essential for HBx activity. The plasmids all synthesize HBx mRNAs containing the adenoviral late 5' noncoding region (tripartite leader), which permits efficient translation under serum-free conditions as used here (reviewed in Schneider, 1996, in Translational Regulation, Cold Spring Harbor Press, Cold Spring Harbor). Thus, these data demonstrate that HBx is capable of activating c-src without serum for a prolonged period of time (24–36 h), and only when located in the cytoplasm. It should be noted that conditioned media from cells expressing HBx for 8 h did not activate c-Src in control cells, excluding the possibility that HBx acts by inducing secretion of autocrine factors. HBx activation of Ras signaling requires Src family kinases.

Src family kinases were shown to be negatively regulated by phosphorylation of a regulatory carboxy-terminal tyrosine by the action of the protein tyrosine kinase C-terminal Src kinase (Csk). Csk specifically phosphorylates the carboxy-terminal tyrosine and returns Src to an inactive state. Therefore, overexpression of Csk can be used as a mechanism to negatively regulate Src and potentially inhibit the ability of HBx to activate the Ras cascade. To test whether HBx activation of the Src family of kinases is required for stimulation of Ras signaling by HBx, Chang cells were transfected at low density: with plasmids expressing HBxo, HBx or HBx and Csk, serum-starved for 20 hours, 2% serum restored for 2 hours to permit protein synthesis, and activation of immunoprecipitated MAP kinase at the end of the Ras-MAP kinase cascade assayed by incubation with myelin basic protein (MBP) and [γ-$^{32}$P]ATP (FIG. 2). Expression of HBx induces a strong activation in the ability of MAP kinase to phosphorylate MBP that is abolished upon co-transfection of HBx with Csk. In contrast, overexpression of Csk only slightly impaired activation of MAP kinase by insulin, indicating that expression of Csk did not generally impair activation of the Ras signaling cascade. Thus, these data clearly demonstrate that HBx requires activation of the Src family of kinases for induction of the Ras signaling cascade.

The results presented in FIG. 2A were obtained in the presence of low serum (2% CS), therefore it was necessary to rule out the possibility that HBx only required Src activation for stimulation of ERK activity in the presence of serum. Furthermore, experiments were conducted to determine whether HBx, without the presence of serum, continued to stimulate ERK MAP kinase activity through the prolonged induction of Src family kinases observed in FIG. 2A. Chang cells were transfected with plasmids expressing HBxo, HBx, or HBx with Csk, kinase-inactive Src (pCMVSK$^-$), or kinase-inactive Fyn (pCMVFK$^-$). Kinase-inactive forms of both Src and Fyn have been shown to act in a dominant inhibitory fashion to impair activation of downstream Src targets and are considered dominant-negative proteins (Rusanescu et al., 1995, supra; Twamley-Stein et al., 1993, supra). Cells were serum-starved in 0.5% CS for 24 hours following transfection, and activation of ERK2 assayed by immunoprecipitation and incubation with MBP and [γ-$^{32}$P]ATP. ERK2 immunoprecipitates obtained from serum-starved cells expressing HBx for 36 hours displayed a 5 to 10 fold increase in kinase activity. Moreover, co-expression of HBx with Csk, SrcK$^-$, and FynK$^-$ impaired activation of ERK2, although activation of ERK2 was inhibited to a lesser extent by SrcK$^-$. Although these results indicate that both Src and Fyn play a role in activation ERK by HBx, the precise contribution that each makes to stimulation of Ras signaling by HBx was not characterized. Nevertheless, these results demonstrate that HBx stimulates a prolonged activation of ERK2 via stimulation of Src family kinases, and does so without a requirement for serum.

A more distant family member of the MAP kinase family, Jun-NH$_2$ terminal kinase (JNK) (Derijard et al., 1994), greatly enhances the transcriptional activity of c-Jun through binding to the c-Jun transactivation domain and phosphorylating it at Ser-63 and Ser-73 (Hibi et al., 1993, Genes Devel. 7:2135–2148). Recent work from our lab has demonstrated that HBx stimulates the activity of the JNK members of the MAP kinase family, through the Ras pathway (Benn et al., 1996 J. Virol 70:4978–4985). Experiments were carried out to determine whether HBx induction of JNK activity occurs through activation of the Src family kinases similar to HBx stimulation of the ERKs. Chang cells were transfected with plasmids expressing HBxo, HBx, HBx and dominant-negative Src (SrcK$^-$), or HBx and dominant-negative Fyn (FynK$^-$), and serum-starved for 24 hours. JNK activity was assayed by immunoprecipitating JNK protein from equal amounts of cell lysate and incubating it with purified GST-c-Jun (1–223), which contains the N-terminal site of phosphorylation, and [γ-$^{32}$P]ATP. Expression of HBx induced a strong (~20 fold), sustained activation of JNK which was not observed with HBxo expression, and was completely inhibited by co-expression with the dominant-negative Src and Fyn plasmids. These results illustrate that sustained induction of JNK activity by HBx occurred through activation of Src family kinases. In contrast, expression of HBx did not alter the steady-state level of JNK1 protein. Taken together, the results confirm that an essential process in HBx induction of the MAP kinase family is its activation of Src family members which in turn activates Ras and downstream ERK and JNK MAP kinases.

HBx Transactivation of Transcription Factor AP-1 Involves Essential Activation of Src Kinases Here it is shown that HBx activation of AP-1 DNA binding activity and AP-1 directed transcription, both involve an essential requirement for HBx activation of Src tyrosine kinases. Chang cells were transfected with plasmids expressing HBx or HBxo proteins, with or without cotransfection of Csk, serum starved and nuclear extracts prepared for electrophoretic mobility shift assay (EMSA) using equal amounts of nuclear extracts and a $^{32}$P-labeled dsDNA probe containing one AP-1 binding site, as described (Benn et al., 1996 supra). Cotransfection of increasing amounts of the Csk expressing plasmid suppressed HBx induction of AP-1 DNA binding complexes in a titratable manner (FIG. 3A). Finally, cells were cotransfected with plasmids expressing HBx or HBxo and an AP-1 dependent luciferase reporter under the control of a minimal promoter, with and without a Csk expression plasmid (FIG. 3B). Co-expression with Csk fully blocked HBx induced activation of AP-1 dependent transcription, again demonstrating that activation of Src kinases is essential for transcriptional transactivation by HBx.

HBx Induces N-Myc and Stimulates Cyclin-dependent Kinases by Activating c-Src The following experiments demonstrate that HBx induction of N-Myc requires HBx activation of Src family kinases. Chang cells were transfected with plasmids expressing HBxo, HBx, Csk, SrcK$^-$, FynK$^-$, and the dominant-negative Ras (RasN17). The Ras N17 mutant was initially shown to preferentially bind GDP in vitro and to inhibit cellular proliferation when stably expressed in NIH 3T3 cells (Feig et al., 1988, Moll. Cell Biol. 8:3235–3243). Transfected cells were serum-starved for 20 hours, nuclear extracts prepared, equal amounts of protein resolved by SDS-PAGE and immunoblotted with anti-N-Myc antibodies. Expression of transfected HBx elevates the amount of N-Myc protein 3–4 fold. Co-expression of HBx with Csk, and to a lesser extent the dominant-negative SrcK$^-$, impaired the increase in N-Myc protein by HBx. The inability of dominant-negative Ras or Fyn proteins to block Src activation is consistent with the report by Barone and Courtneidge (1995, supra). Co-expression of HBx with the dominant-negative Ras had no effect on induction of N-Myc by HBx, and neither did the expression of dominant-negative Fyn protein. Whether other Src family members (e.g. Yes or Lyn) are involved in N-Myc induction by HBx was not tested in these experiments. These data indicate that HBx elevation of N-Myc occurs through a c-Src-dependent, Ras-independent pathway.

7. EXAMPLE

The HBx Protein Promotes Prolonged WHV Replication in Chang Cells

Conflicting results have been reported as to the requirement for HBx during the viral life cycle in cultured cells. While one group found no dependence on HBx for either the synthesis of HBV DNA or virion export in Huh7 and HepG2 cells (Blum et al., 1992 J. Virol. 66: 1223–1227), others have reported that genomic DNAs containing a wild-type HBx protein produce elevated levels of replicated viral DNA (Yaginuma et al., 1987 Proc. Natl. Acad. Sci. 84:2678–2682; Zoulim et al., 1994 J. Virol. 68:2026–2030). In order to determine the validity of studying the activities of HBx in the WHV system, the following analyses were conducted.

7.1 Materials and Methods

Southern Blot Analysis of Viral Core-associated DNA

Chang cells were transfected with infectious WHV clones, (2×10 cm plates) were washed twice with PBS and lysed in 500 μl lysis buffer/10 cm plate (20 mM Tris HCl pH 7.5, 1 mM EDTA, 100 mM NaCl, 0.5% NP-40) for 10–15 minutes. Lysates were centrifuged at 12,000×g for 30 minutes, MgCl$_2$ was adjusted to 10 mM, DNAseI (Boehringer Mannheim) was added to 20 U /ml and the lysates were incubated at 37° C. for 2 hours. Following DNAse I treatment, the lysates were centrifuged for 5 min at 12,000×g, layered onto a 20% sucrose cushion (300 μl of 20% sucrose in 20 mM Tris HCl pH 8.0, 150 mM NaCl) and centrifuged for 178,000×g for 3 hours at 20° C. The pellet was then resuspended in 250 μl digestion buffer (10 mM Tris HCl pH 7.5, 10 mM EDTA, 1%-SDS, 1 mg/ml proteinase K [Boeringer Mannheim]) and digested for 16–20 hours at 37° C. After extracting once with phenol and twice with phenol:CHCl$_3$, 100 μl H$_2$O was added and the core-associated DNA precipitated using 0.2 M NaCl/2½ vol. ethanol and resuspended in 20 μl TE (10 mM Tris HCl pH 7.5, 1 mM EDTA). 10 μl DNA/lane was electrophoresed through a 1.2% agarose gel and transferred to Duralon UV membrane (Stratagene). The filters were pre-hybridized at 42° C. in 50% formamide, 5×SSC, 2.5×Denhardts, 0.1% SDS, 1 mM EDTA, 5 mM NaH$_2$PO$_4$, and 100 μg/ml salmon sperm DNA for 3–24 hours, then hybridized in the same solution to a radiolabeled probe prepared from full length pWHV, HindIII digested and labeled to high specific activity with [α-$^{32}$P] dGTP and [α-$^{32}$P] dCTP. Hybridization was for 24–72 hours at 42° C. (Sambrook et al., 1989, supra). The filters were washed at room temperature three times with 1× SSC, 0.1% SDS, three times at 50° C. with 0.1×SSC, 0.1% SDS and autoradiographed for 1–2 days at −70° C.

Northern Analysis

Chang cells were washed twice with PBS and total RNA prepared according to the manufacturer's instructions (RNeasy mini kit; Qiagen). 15 μg total RNA per sample were resolved through a 1.2% formaldehyde-agarose gel (Sambrook et al., 1989, supra), transferred to Duralon UV membrane, and pre-hybridized in Quick-Hyb solution (Stratagene) at 65° C. Hybridization to 32P-labeled full length WHV probe was carried out in the same solution at 65° C., washed as described above, and autoradiographed for 1 day.

7.2 Results

To assess the requirement for the HBx protein during WHV replication in Chang cells, transfection experiments were carried out using either a replication-competent cDNA of WHV that expresses the wild-type WHx (wtWHV), or a replication-impaired cDNA which expresses a C-terminally deleted (inactive) WHx mutant (pXWHV). wtWHV and pCWHV encode a cDNA corresponding to the viral pregenomic RNA which is driven by the CMV promoter. While wtWHV directs the expression of infectious WHV in tissue culture cells and can initiate a productive infection when implanted into the livers of susceptible woodchucks, pCWHV is non infectious in animals (Zoulim et al., 1994, supra). Chang cells were transfected at low confluency (see Methods) with plasmids encoding either wtWHV or PCWHV and the transfected cells were passaged when confluent and propagated in culture for 11 days. To purify viral intracellular core-associated DNA, equal amounts of transfected cells were lysed in 0.5% NP-40, centrifuged through a 20% sucrose cushion, isolated viral cores were incubated with SDS and Proteinase K, and the viral core-associated DNA was purified by phenol extraction and ethanol precipitation. The purified viral DNA was electrophoresed through a 1.2% agarose gel, transferred to nylon membrane, and a Southern blot analysis was carried out by hybridization of the viral DNA to a $^{32}$P-labeled full-length genomic WHV DNA probe (FIG. A). As compared to the almost undetectable level of core associated-DNA purified from cells transfected with pCWHV (HBx mutant), the abundance of core-associated DNA isolated from wtWHV transfected cells was strongly enhanced by ~20–30 fold.

The hepadnavirus replication scheme discussed earlier dictates that the DNA purified from viral core particles can exist in several different forms which correspond to different stages of genomic maturation. These forms include abundant free minus strands, rare linear DNA duplexes and substantial amounts of mature, relaxed duplex DNA species (Ganem, 1996 In Fields Virology, B. N. Fields, D. M. Knipe and P. M. Howley, eds. (Philadelphia:Lippincott Publishers) pp. 2703–2737). The presence of various forms of DNA within viral cores therefore reflects the presence of ongoing viral replication. The DNA isolated from wtWHV-expressing cells appeared to contain both relaxed circular and single-stranded forms, indicating active replication. Furthermore, these results demonstrated that WHV was able to maintain a replicative life cycle at least over the course of 11 days in Chang cells.

In comparison, HepG2 cells were also transfected with wt WHV, pCWHV, and pAUGWHV plasmids. PAUGWHV contains a mutation of the first AUG to a WUG in the WHx ORF, rendering the X mRNA incapable of synthesizing WHx protein. Like pCWHV, pAUGWHV is non-infectious in animals (Zoulim et al., 1994). Transfected HepG2 cells were propagated for 14 days, the intracellular viral core-associated DNA was purified as described above, and the viral DNA subjected to Southern blot hybridization to a $^{32}$P-labeled full-length WHV genomic probe (FIG. 4B).

The presence of the HBx protein enhanced the abundance of WHV core-associated DNA, although the upregulation of viral DNA synthesis by WHx (~5 fold) was not nearly as pronounced as that observed in Chang cells (FIG. 4A). To further confirm that the strong increase in the abundance of viral DNA replicative DNA intermediates in the presence of WHx is due solely from expression of the HBx protein, experiments were carried out to assess whether HBx protein expressed in trans could complement the pCWHV defect in viral DNA synthesis shown in FIG. 4A. Chang cells were cotransfected with either pCWHV and pCMV-HBxo, or with pCWHV and pCMV-HBx, intracellular viral cores were isolated 3 days post-transfection, and the core-associated DNA analyzed by Southern blot analysis as described above (FIG. 5). Expression of HBx in trans complemented the pCWHV deficiency in viral DNA synthesis, although HBx trans-complementation did not entirely restore viral DNA synthesis to wild type levels (compare wt WHV in FIG. 4A to FIG. 5). This discrepancy may result from a different level of expression of the HBx protein from pCMV-HBx as compared to expression from the wtWHV genomic DNA, or possibly unequal transfection efficiencies. Regardless, these results establish that HBx can trans-complement PCWHV replication. These data also show that expression of the HBV HBx protein restored the ability of PCWHV to synthesize viral DNA intermediates, indicating that HBx and WHx are functionally interchangeable.

8. EXAMPLE

HBx Stimulates SRC-Ras Signaling During in Vitro Viral Replication

The following analysis was conducted to determine if HBx activates Src-Ras signaling when expressed in the context of in vitro viral replication (i.e., in tissue culture cells).

In these studies, HBV replication was supported in Chang cells with head-to-tail HBV dimers. Previous studies showed that transfection of either closed circular HBV DNA (Sureau et al., 1986 Cell 47:37–47) or HBV DNA in which two copies of the genome have been arranged in a head-to-tail dimer (HTD) can support in vitro production of viral proteins, synthesis of DNA replicative intermediates, and export of virions in permissive cells (Blum et al., 1992, J. Virol. 66:1223–1227; Yaginuma et al., 1987, Proc. Natl. Acad. Sci. 84:2678–2682). Due to the overlapping nature of the ORFs found in the circular genome of HBV, plasmids containing only one copy of the HBV genome interrupt viral coding regions, do not produce viral proteins and will not replicate (Dubois et al., 1980). These studies were conducted to directly determine whether HBx activates Ras signaling when synthesized from a genomic HBV HTD.

8.1 Materials and Methods

The experiments were conducted using the materials and methods described in Sections 6.1 and 7.1 infra.

8.2 Results

To determine whether WHx also requires activation of Src family kinases for stimulation of Ras signaling during ongoing viral replication, Chang cells were co-transfected with plasmids synthesizing wtWHV and dominant-negative Ras (RasDN), dominant-negative Src (SrcK$^-$), or Csk proteins, and activation of MAP kinase was measured. As a control, Chang cells were also transfected with the WHx mutant plasmid, pCWHV. Eighteen hours post-transfection, cells were serum-starved for 24 hours, MAP kinase (ERK2) was immunoprecipitated from equal amount of cell lysate, and the immunoprecipitated protein was incubated with MBP and [γ$^{32}$P]ATP (FIG. 6). Consistent with our results described infra, wt WHV but not pCWHV strongly elevated the phosphotylation of MBP by MAP kinase. This indicates that the HBx protein stimulates Ras signaling during active viral replication. Furthermore, co-expression of wtWHV with either Ras or Src dominant-negative proteins, or with Csk protein, efficiently inhibited downstream activation of MAP kinase. These results indicate that the HBx protein activates a Src-Ras signaling cascade during active viral replication in cultured cells. Furthermore, co-expression of wtWHV with either the Ras or Src dominant-negative proteins, or with Csk protein, efficiently inhibited downstream activation of MAP kinase, indicating that the HBx protein activated a Src-Ras signaling cascade during in vitro viral replication.

9. EXAMPLE

WHV Requires SRC Family Kinases for in vitro Replication

Given our observations described infra that HBx activates a Src-Ras signaling cascade during viral replication in vitro, and that the activation Src kinases by HBx mediated both Ras activation and cell cycle progression, experiments were next carried out to determine whether HBx activation of Src is an essential function during viral replication.

9.1 Materials and Methods

The experiments were conducted using the methods and materials described in Sections 6.1 and 7.1 infra.

9.2 Results

Chang cells were co-transfected with plasmids encoding either wtWHV, pCWHV, wtWHV and RasDN, or wtWHV and Csk, intracellular core-associated viral DNA was isolated 3 days post-transfection, and purified viral DNA analyzed by Southern blot hybridization as described above (FIG. 7). Consistent with the previous data, accumulation of viral DNA replicative intermediates was strongly enhanced in cells expressing wtWHV, as compared to cells expressing pCWHV. Co-expression of RasDN protein with wtWHV had no detectable effect on viral replication, and viral DNA was synthesized at near wild-type levels. Expression of the RasDN protein impaired WHV activation of MAP kinase under these same experimental conditions (FIG. 7), indicating that the RasDN protein was able to function during WHV replication. However, these results illustrate the effects of one particular inhibitor of Ras and do not provide an explanation of the mechanism by which activation of Src kinase supports HBV replication. In sharp contrast, co-expression of Csk with wtWHV completely abolished the ability of wtWHV to replicate to high levels. These results demonstrated that an essential component of the requirement of HBx during in vitro viral replication in Chang cells is its ability to activate Src signaling cascades, and that activation of Src family kinases has a critical role during the viral replicative life cycle.

It was next addressed whether the stimulation of viral replication by WHx was a result of transcriptional transactivation of WHV genes by WHx. Chang cells were transfected with wtWHV or pCWHV plasmids. Total cellular RNA was isolated 4 days post-transfection, equal amounts of RNA were resolved by electrophoresis through a 1.2% formaldehyde-agarose gel, and the viral mRNAs were visualized by Northern blot analysis using a $^{32}$P-labeled probe corresponding to the entire WHV genome (FIG. 8, lanes 1 and 4). Steady-state levels of the genomic viral mRNAs was enhanced ~3–5 fold in Chang cells expressing wtWHV as compared to PCWHV. These data suggest that HBx protein induced only a moderate increase in the amount of viral mRNA, which cannot account for its striking stimulation of viral replication.

To assess whether HBx activation of a Src signaling cascade plays an essential role in transcriptional upregulation of the viral mRNAs, Chang cells were co-transfected with wtWHV and either RasDN or Csk plasmids, and the RNA visualized by Northern analysis (FIG. 7, lanes 2 and 3). Co-expression of RasDN with wtWHV only slightly reduced the amount of the RNA species, while co-expression of wtWHV with Csk reduced the RNA level ~3–5 fold, to the level also observed by expression of PCWHV. To ensure that the decrease in synthesis of WHV RNA by Csk was not the unforseen consequence of Csk inhibition of the CMV promoter (which drives synthesis of the WHV pregenomic RNA), control experiments assessing the effect of Csk on a CMV-βgal reporter were carried out. In comparison with expression of CMV-βgal alone, co-expression of Csk with CMV-βgal did not significantly alter expression of the βgal protein as measured by its β-galactosidase activity (Sambrook et al, 1989, supra). This control experiment indicates that expression of Csk does not generally inhibit transcription of the CMV promoter, and rules out a non-specific effect of Csk on viral transcription. Therefore, these data suggest that the HBx protein moderately increases the abundance of all the viral transcripts through activation of the Src family of kinases. However, the WHx-induced increase in mRNA abundance (~3–5 fold) is much less then the HBx-induced increase in viral DNA synthesis (~20–30 fold). Therefore, transcriptional transactivation by HBx does not appear to fully account for the augmentation of viral replication by the HBx protein. The stimulation of Src signaling cascades by HBx must therefore promote WHV replication independent of the effect of WHx on viral transcription. These results illustrate that HBx activates a Src-Ras signaling cascade during viral replication in vitro which is essential for the host cell to sustain HBV replication.

10. EXAMPLE

WHV Requires SRC Family of Kinases for in vitro Replication

The requirement for activation of Src kinase family members in replication of WHV can be determined in woodchuck infected livers in the following manner. A 2–5 year old woodchuck is experimentally infected using a pooled serum from previous chronic carrier woodchucks. After 2 years of chronic infection, determined by WHsAg ELISA, the infected liver is surgically removed, the liver is perfused as described (Jacob et al., 1994, Exp. Cell Res. 212:42–48), hepatocytes are dispersed by collagenase treatment and plated onto collagen coated dishes in L15 medium supplemented with 5% fetal calf serum, hydrocortisone and insulin. To introduce an inhibitor of Src kinases into primary hepatocytes, the Csk gene is cloned into the left-end of a replication-defective adenovirus vector under the control of the CMV promoter, as described (Doria et al., 1995, EMBO J. 14:4747–4757). Adenovirus vectors infect primary cells and express trans-genes efficiently, whereas it is not possible to transfect such cells at a high rate. Within several days of plating, cells are infected with the Csk-adenovirus vector, medium is replaced with L15 medium lacking insulin and containing reduced serum (between 0.5–2%). Cells are then harvested at 2 and 4 days after introduction of the vector. The medium can be assayed for levels of secreted WHV by ELISA for WHcAg and WHsAg. The level of virus replication can be assayed as described for Chang cells.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A method for treating Hepatitis B virus (HBV) infection or inhibiting HBV virus replication comprising administering a compound to an HBV-infected patient that decreases the activity of Src kinase.

2. A method for inhibiting Hepatitis B virus (HBV) infection or replication, comprising administering a Csk protein to decrease the activity of Src kinase in a subject.

3. The method of claim 1 wherein the compound that inhibits Src kinase activity is a tyrphostin inhibitor or a pharmaceutically acceptable salt thereof.

4. The method of claim 1 wherein the compound that inhibits Src kinase activity is a pyrozolopyrimidine or a pharmaceutically acceptable salt thereof.

5. The method of claim 1 wherein the compound that inhibits Src kinase activity is benzylidenemalononitrile or a pharmaceutically acceptable salt thereof.

6. The method of claim 1 wherein the compound that inhibits Src kinase activity is angelmicin or a pharmaceutically acceptable salt thereof.

7. The method of claim 1 wherein the compound that decreases the activity of Src kinase is determined by an in vitro assay comprising:
   a) contacting a Src kinase with the compound; and
   b) determining whether the level of Src kinase activity is reduced in the presence of the compound as compared to the level of Src kinase activity in the absence of the compound.

8. The method of claim 1 wherein the compound that decreases the activity of Src kinase is determined by an in vitro assay comprising:
   a) contacting cells expressing Src kinase with the compound;
   b) determining whether the level of Src kinase activity is reduced in those cells contacted with the compound as compared to that level of Src kinase activity in said cells in the absence of the compound.

9. The method of claim 1 wherein the compound that decreases the activity of Src kinase is determined by an in vitro assay comprising:
   a) contacting a cell expressing HBx with the compound;
   b) determining whether the level of Src kinase activity is reduced in those cells contacted with the compound as compared to the level of Src kinase activity in cells expressing HBx in the absence of the compound.

* * * * *